United States Patent
Nallathamby et al.

(10) Patent No.: US 12,161,725 B2
(45) Date of Patent: Dec. 10, 2024

(54) PHAGE MIMICKING NANOPARTICLES

(71) Applicant: UNIVERSITY OF NOTRE DAME DU LAC, South Bend, IN (US)

(72) Inventors: Prakash Daniel Nallathamby, Granger, IN (US); Juliane Hopf, Granger, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 875 days.

(21) Appl. No.: 17/269,710

(22) PCT Filed: Nov. 7, 2019

(86) PCT No.: PCT/US2019/060202
§ 371 (c)(1),
(2) Date: Feb. 19, 2021

(87) PCT Pub. No.: WO2020/097288
PCT Pub. Date: May 14, 2020

(65) Prior Publication Data
US 2021/0252162 A1    Aug. 19, 2021

Related U.S. Application Data

(60) Provisional application No. 62/757,086, filed on Nov. 7, 2018, provisional application No. 62/869,648, filed on Jul. 2, 2019.

(51) Int. Cl.
| | |
|---|---|
| *A61K 47/00* | (2006.01) |
| *A61K 33/242* | (2019.01) |
| *A61K 33/38* | (2006.01) |
| *A61K 47/69* | (2017.01) |
| *B82Y 5/00* | (2011.01) |
| *B82Y 30/00* | (2011.01) |
| *B82Y 40/00* | (2011.01) |

(52) U.S. Cl.
CPC ........ *A61K 47/6929* (2017.08); *A61K 33/242* (2019.01); *A61K 33/38* (2013.01); *A61K 47/6923* (2017.08); *B82Y 5/00* (2013.01); *B82Y 30/00* (2013.01); *B82Y 40/00* (2013.01)

(58) Field of Classification Search
CPC .............. A61K 47/6929; A61K 33/242; A61K 33/38; A61K 47/6923; B82Y 5/00; B82Y 30/00; B82Y 40/00
See application file for complete search history.

(56) References Cited

U.S. PATENT DOCUMENTS

| | | |
|---|---|---|
| 9,320,719 B2 | 4/2016 | Messersmith et al. |
| 9,724,279 B2 | 8/2017 | Shieh |
| 2003/0108612 A1 | 6/2003 | Xu et al. |
| 2010/0047546 A1 | 2/2010 | Malshe et al. |
| 2012/0021034 A1 | 1/2012 | Zink et al. |
| 2017/0232109 A1 | 8/2017 | Mirkin et al. |

FOREIGN PATENT DOCUMENTS

| | | |
|---|---|---|
| KR | 1020130042363 A | 4/2013 |
| KR | 1020130118086 A | 10/2013 |
| WO | 2008/064750 A2 | 6/2008 |
| WO | 2017/145167 A1 | 8/2017 |
| WO | 2017/161296 A1 | 9/2017 |

OTHER PUBLICATIONS

Abedon, Stephen T., et al. Phage therapy past, present and future. Frontiers in microbiology 8 (2017) 981.
Amirthalingam "Use of Silica-Gold Core Shell Structured Nanoparticles for Targeted Drug Delivery System" Nanomedicine & Nanotechnology, 2011, vol. 2, pp. 1-5.
Demain, Arnold L., et al. "Microbial degradation of cephalosporin C." Nature 199.4896 (1963): 909-910.
Dong, W., Mao, X., Guan, Y. et al. Antimicrobial and anti-inflammatory activities of three chensinin-1 peptides containing mutation of glycine and histidine residues. Sci Rep 7, 40228 (2017).
Fields, Francisco R., et al. "Rational design of syn-safencin, a novel linear antimicrobial peptide derived from the circular bacteriocin safencin AS-48." The Journal of antibiotics 71.6 (2018): 592-600.
Gisby, John, and Joanna Bryant. "Efficacy of a new cream formulation of mupirocin: comparison with oral and topical agents in experimental skin infections." Antimicrobial agents and chemotherapy 44.2 (2000): 255-260.
Kostopoulou, Athanasia, et al. Iron oxide colloidal nanoclusters as theranostic vehicles and their interactions at the cellular level. Nanomaterials 8.5 (2018) 315.
Kuehn, Bridget. "Evolution of "Nightmare Bacteria"." Jama 319.20 (2018): 2070-2070.
Kugelberg, Elisabeth, et al. "Establishment of a superficial skin infection model in mice by using *Staphylococcus aureus* and *Streptococcus pyogenes*." Antimicrobial agents and chemotherapy 49.8 (2005): 3435-3441.
Lin DM, Koskella B, Lin HC. Phage therapy An alternative to antibiotics in the age of multi-drug resistance. World J Gastrointest Pharmacol Ther. 2017;8(3)162-173. doi10.4292wjgpt.v8.13.162.
Mansour, Sarah C., et al. "Bacterial abscess formation is controlled by the stringent stress response and can be targeted therapeutically." EBioMedicine 12 (2016): 219-226.
Matsumoto, Ryo, et al. "Effects of the properties of short peptides conjugated with cell-penetrating peptides on their internalization into cells." Scientific reports 5.1 (2015): 1-9.
Nallathamby, Prakash D., et al. "New surface radiolabeling schemes of super paramagnetic iron oxide nanoparticles (SPIONs) for biodistribution studies." Nanoscale 7.15 (2015): 6545-6555.

(Continued)

*Primary Examiner* — Jeanette M Lieb
(74) *Attorney, Agent, or Firm* — Workman Nydegger

(57) ABSTRACT

An antibacterial nanoparticle (ANP) and related methods and antibacterial medical products are disclosed. An ANP includes a silica core with a plurality of gold nanospheres conjugated thereto and at least some of the gold nanospheres being silver-coated gold nanospheres. Iron oxide nanospheres may also be conjugated to the silica core, and at least some of the silver-coated gold nanospheres, or iron oxide nanospheres, if present, can be conjugated to one or more polycationic polymers and/or one or more antibacterial peptides.

15 Claims, 15 Drawing Sheets

Specification includes a Sequence Listing.

(56) References Cited

OTHER PUBLICATIONS

Nallathamby, Prakash D., et al. "Preparation of fluorescent Au-SiO2 core-shell nanoparticles and nanorods with tunable silica shell thickness and surface modification for immunotargeting." Journal of Materials Chemistry B 4.32 (2016): 5418-5428.

Nerambourg, Nicolas, et al. "Quenching of molecular fluorescence on the surface of monolayer-protected gold nanoparticles investigated using place exchange equilibria." Langmuir 23.10 (2007): 5563-5570.

Nishida, Minoru, et al. "Studies on Microbial Degradation of Cephalosporin C Derivatives. I the Role of ß-Lactamase and Acylesterase in the Enzymatic Degradation of Cephalosporins." The Journal of antibiotics 21.3 (1968): 165-169.

Norman H. Olson, Timothy S. Baker, Peter Willingmann, Nino L. Incardona, The three-dimensional structure of frozen-hydrated bacteriophage FX174, Journal of Structural Biology, vol. 108, Issue 2, 1992, pp. 168-175.

Prestinaci, Francesca, Patrizio Pezzotti, and Annalisa Pantosti. "Antimicrobial resistance: a global multifaceted phenomenon." Pathogens and global health 109.7 (2015): 309-318.

Revista mexicana de ingeniería química, Mexico, 2014 vol. 13 No. 2 Ago, p. 555-561.

Ross, G. W., et al. "Degradation of selected cephalosporins by homogenates of the alimentary tract of rats." Journal of medical microbiology 3.3 (1970): 511-519.

Shankar, P Ravi.Archives of Pharmacy Practice; Selangor vol. 7, Iss. 3, (Jul.-Sep. 2016): 110-111.

Sulakvelidze, Alexander, Zemphira Alavidze, and J. Glenn Morris. "Bacteriophage therapy." Antimicrobial agents and chemotherapy 45.3 (2001): 649-659.

Sung, Yulung, Fernando Campa, and Wei-Chuan Shih. "Open-source do-it-yourself multi-color fluorescence smartphone microscopy." Biomedical optics express 8.11 (2017): 5075-5086.

Tsai "Antibacterial Cellulose Paper Made with Silver-Coated Gold Nanoparticles" Scientific Reports, 2017, vol. 7, pp. 1-10.

Ventola, C Lee. "The antibiotic resistance crisis: part 1: causes and threats." P & T : a peer-reviewed journal for formulary management vol. 40,4 (2015): 277-83.

Wang "Functionalized nanoparticles complexed with antibiotic efficiently kills MRSA and other bacteria" Chem Commun, 2014, vol. 50, pp. 12030-12033.

Zaman, Sojib Bin et al. "A Review on Antibiotic Resistance: Alarm Bells are Ringing." Cureus vol. 9,6 e1403. Jun. 28, 2017, doi:10.7759/cureus.1403.

Zhai, Le, et al. "Triazolylthioacetamide: A valid scaffold for the development of New Delhi metallo-ß-lactmase-1 (NDM-1) inhibitors." ACS medicinal chemistry letters 7.4 (2016): 413-417.

Morales-Avila, E et al. "Antibacterial Efficacy of Gold and Silver Nanoparticles Functionalized with the Ubiquicidin 29-41 Antimicrobial Peptide." Journal of Nanomaterials. Mar. 26, 2017, vol. 2017, Article ID 5831959; pp. 1-10; abstract; p. 7, 2nd column, 2nd paragraph; DOI:https://doi.org/10.1155/2017/5831959.

Lee, B et al. "Antimicrobial peptide-loaded gold nanoparticle-DNA apatmer conjugates as highly effective antibacterial therapeutics against Vibrio vulnificus." Scientific Reports. Oct. 19, 2017, vol. 7, No. 13572; pp. 1-10; DOI: 10.1038/s41598-017-14127-z.

Yuan, K. et al. "Anitmicrobial peptide based magnetic recognition elements and Au@Ag-Gosers tags with stable internal standars: a three in one biosensor for isolation, discrimination and killing multiple bacteria in whole blood." Chemical Science. Nov. 2, 2018, vol. 9, No. 47; pp. 8781-8795; DOI: 10.1039/c8sc04637a.

Badawy et al., "Surface charge-dependent toxicity of silver nanoparticles", Environ Sci Technology, 2011, vol. 45, No. 1, pp. 283-287.

Banerjee et al., "Enhanced antibacterial activity of bimetallic gold-silver core-shell nanoparticles at low silver concentration", Nanoscale, 2011, vol. 3, pp. 5120-5125.

Kumari et al., "Deposition of silver and gold nanoparticles on surface engineered silica particles and their potential applications", J Nanoscience Nanotechnology, Oct. 2012, vol. 12, No. 10, pp. 8001-8007.

Lambadi et al., "Facile biofunctionalization of silver nanoparticles for enhanced antibacterial properties, endotoxin removal, and biofilm control", International Journal of Nanomedicine, Mar. 18, 2015, vol. 10, pp. 2155-2171.

ANPs@MC1-2
medium silver

ANPs@MC1-2
high silver

PHAGE MIMICKING NANOPARTICLES

CROSS-REFERENCE TO RELATED APPLICATIONS

This application claims priority to PCT Application No. PCT/US2019/060202 filed Nov. 7, 2019, entitled "PHAGE MIMICKING NANOPARTICLES", which claims priority to and the benefit of U.S. Provisional Patent Application No. 62/757,086 filed Nov. 7, 2018 entitled "PHAGE MIMICKING NANOPARTICLES" and priority to and the benefit of U.S. Provisional Patent Application No. 62/869,648 filed Jul. 2, 2019 entitled "PHAGE MIMICKING NANOPARTICLES". Each of the aforementioned applications are incorporated herein by reference in their entirety.

BACKGROUND OF THE INVENTION

Technical Field

The present disclosure relates generally to silica core nanoparticles. More specifically, the present disclosure relates to silica core nanoparticles with antibacterial properties.

Background and Relevant Art

The pathogens *Enterococcus faecium, Staphylococcus aureus, Klebsiella pneumoniae, Acinetobacter baumannii, Pseudomonas aeruginosa,* and *Enterobacter* species (often referred to as the ESKAPE pathogens) are a leading cause of nosocomial bacterial infections, which often result in chronic, skin, or high-density biofilm infections that are difficult to treat by reason of their virulence and adaptivity (particularly in the geriatric population). The ESKAPE pathogens often exhibit multidrug resistance to most or sometimes all available classes of antibiotics. Antibiotic discovery and development are stagnating and unable to keep pace with the adaptive multidrug resistance of many pathogens. Absent another solution, antibiotic-resistant bacterial strains are poised to cause widespread, untreatable infections, and presently treatable infections, such as pneumonia, tuberculosis, gonorrhea, and *salmonellosis,* could become more difficult to treat thereby increasing the morbidity and/or mortality rate associated with these infections.

The use of nanomaterials as antibacterial alternatives to antibiotics has shown promise owing to their unique physical and chemical properties. Nanoparticles are typically below 100 nm in size and exhibit a high surface-to-volume ratio, giving them the potential to closely interact with microbial membranes. Specifically, the use of metal and metal oxide nanoparticles as a new class of antibacterial agents have received increased attention over the last decade due to their bactericidal properties. For example, Zinc oxide nanoparticles can inhibit the growth of *S. aureus* by a combination of mechanisms (e.g., induction of oxidative stress, cell membrane disruption, and/or the release of heavy metals).

Although bacterial resistance to metal nanoparticles is less likely, bacteria have been known to utilize efflux pumps to effectively rid themselves of nanoparticles, reducing the antibacterial effects of such nanoparticles. Furthermore, some nanoparticles are toxic to eukaryotic cells, which further limits their therapeutic dosage window.

Accordingly, there is an urgent need for broad-spectrum antibacterial agents, independent of antibiotics, to effectively prevent the progression of antibiotics resistance and to provide the necessary alternative to fight infectious diseases.

SUMMARY OF INVENTION

Embodiments of the present disclosure are directed to antibiotic-free strategies to fight infectious diseases and to combat antibiotic resistance. Disclosed embodiments include antimicrobial nanoparticle-based systems that structurally mimic the capsid structure and/or density distribution of protein turrets on the head of bacteriophages and can act to primarily inhibit bacterial growth and in some cases kill pathogenic bacteria.

For example, disclosed antibacterial nanoparticles (ANPs) include a silica core and a plurality of gold nanospheres conjugated to (or immobilized on) the silica core. At least some of the gold nanospheres are coated with a layer of silver. Iron oxide nanospheres may also be conjugated to the silica core.

In one aspect, the gold nanospheres, or iron oxide nanospheres, if any, are conjugated to the silica core such that a surface density of the gold nanospheres, and/or iron oxide nanospheres, if any, is at least 60% similar to a surface density of protein turrets on a bacteriophage, preferably above 80%.

In one aspect, at least some of the plurality of gold nanospheres, or at least some of the plurality of iron oxide nanospheres, if any, are conjugated to one or more polycationic polymers.

In one aspect, at least some of the gold nanospheres or iron oxide nanospheres, if any, are conjugated to one or more antibacterial peptides, such as Mutant chensinin-1-2 having amino acid sequence SAVWRWRRFWLRKRK, corresponding to SEQ ID NO: 1; synthetic safencin-20 having amino acid sequence AWKKTIRQYLKNKIKKKGRKAVIAW, corresponding to SEQ ID NO: 2; synthetic safencin-96 having amino acid sequence AWKEKIRKKLKNEIKKKWRKAVIAW, corresponding to SEQ ID NO: 3; synthetic safencin having amino acid sequence AGKETIRQYLKNEIKKKGRKAVIAW, corresponding to SEQ ID NO: 4; peptide 20 having amino acid sequence AWKKTIRQYLKNKIKKKGRKAVIAW, corresponding to SEQ ID NO: 5; peptide 52 having amino acid sequence AGKKTIRQYLKNKIKKKWRKAVIAW, corresponding to SEQ ID NO: 6; peptide 60 having amino acid sequence AGKKTIRQYLKNKIKKKGRKWVIAW, corresponding to SEQ ID NO: 7; peptide 90 having amino acid sequence AWKKTIRQYLKNEIKKKWRKAVIAW, corresponding to SEQ ID NO: 8; peptide 91 having amino acid sequence AWKETIRQYLKNKIKKKWRKAVIAW, corresponding to SEQ ID NO: 9; peptide 92 having amino acid sequence AWKKTIRQYLKNKIKKKWRKAVIAW, corresponding to SEQ ID NO: 10; peptide 93 having amino acid sequence AWKEKIRQYLKNEIKKKWRKAVIAW, corresponding to SEQ ID NO: 11; peptide 94 having amino acid sequence AWKETIRKYLKNEIKKKWRKAVIAW, corresponding to SEQ ID NO: 12; and/or peptide 96 having amino acid sequence AWKEKIRKKLKNEIKKKWRKAVIAW, corresponding to SEQ ID NO: 13.

In one aspect, a cell penetrating peptide is anchored to at least some of the iron oxide nanospheres.

In one aspect, the antibacterial nanoparticle also includes a fluorescein molecule anchored to the (silver-coated) gold nanospheres (e.g., by degradable or non-degradable linkers).

Embodiments of the present disclosure additionally include an antibacterial medical product having a plurality of antibacterial nanoparticles disposed on a medical implant, such as a permanent implant or a temporary implant, a dental implant, or a surgical instrument. In one aspect, antibacterial nanoparticles are added to a topological cream.

This summary is provided to introduce a selection of concepts in a simplified form that are further described below in the detailed description. Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 6A is a graph of cell viability using various nanoparticles: $SiO_2$, $SiO_2$@Au, $SiO_2$@Au@Ag with low silver coating (LS), $SiO_2$@Au@Ag with medium silver coating (MS), $SiO_2$@Au@Ag with high silver coating (HS) at both low concentration (LC) and high concentration (HG) and for various $SiO_2$ core sizes (65 nm and 130 nm); FIG. 6B illustrates antibacterial nanoparticles (ANPs), $SiO_2$@Au@Ag, of various $SiO_2$ core sizes conjugated to mutant chensinin-1-2 (MC1-2) with various silver coating thicknesses (LS, MS, HS) and at various concentrations (LC, HC); FIG. 6C graphically illustrates cell viability after treatment with antibacterial nanoparticles (ANPs), $SiO_2$@Au@Ag, of various $SiO_2$ core sizes conjugated to synthetic safencin-20 (Syn20) with various silver coating thicknesses (LS, MS, HS) and at various concentrations (LC, HC); FIG. 6D illustrates cell viability following treatment with antibacterial nanoparticles (ANPs), $SiO_2$@Au@Ag, of various $SiO_2$ core sizes conjugated to synthetic safencin-96 (Syn96) with various silver coating thicknesses (LS, MS, HS) and at various concentrations (LC, HC);

DETAILED DESCRIPTION OF THE PREFERRED EMBODIMENTS

Figure 1:
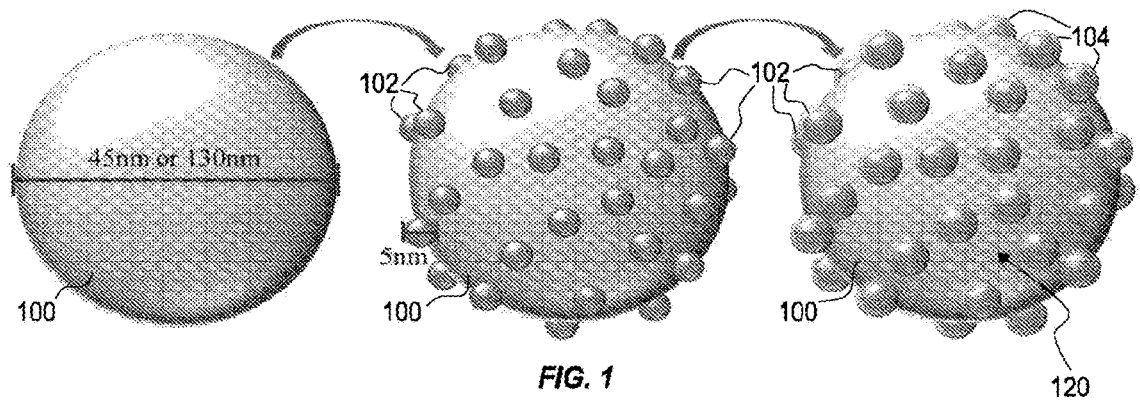
FIG. 1 illustrates a conceptual representation of an antibacterial nanoparticle of the present disclosure, as well as a conceptualization of a method for creating an antibacterial nanoparticle, according to the present disclosure.

Before describing various embodiments of the present disclosure in detail, it is to be understood that this disclosure is not limited to the parameters of the particularly exemplified systems, methods, apparatus, products, kits, and/or processes, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Unless defined otherwise, all technical and scientific terms used herein have the same meaning as commonly understood by one of ordinary skill in the art to which the present disclosure pertains.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, modules, devices, methods, and/or terminology.

As described briefly above, the increasing frequency of nosocomial infections caused by antibiotic resistance strains of bacteria in conjunction with the stagnated discovery of new classes of antibiotics has led to a race against time for the development of new antibacterial agents. In addition to acquisition of genomic antibiotic resistance cassettes, many bacterial strains can form thick mono- or polyclonal biofilms (e.g., at interfaces between medical implants and muscle, bone, or other tissue) that provide a structural and/or biochemical protection against most known antibiotics.

The use of nanomaterials as antibacterial alternatives to antibiotics has shown promise, owing to their unique physical and chemical properties. Nanoparticles are typically below 100 nm in size and exhibit a high surface-to-volume ratio, giving them the potential to closely interact with microbial membranes. Specifically, the use of metal and metal oxide nanoparticles as a new class of antibacterial agents have received increased attention over the last decade due to their bactericidal properties. However, bacteria have been known to utilize efflux pumps to effectively rid themselves of nanoparticles, reducing the antibacterial effects of such nanoparticles. Furthermore, some nanoparticles are highly toxic to eukaryotic cells, which further limits their therapeutic dosage window.

There is an outstanding need in the industry for antibacterial alternatives to the canonical antibiotics, and there is an additional need for improved nanoparticles that can combat antibiotic resistant bacterial strains and/or biofilm formation in a clinical setting.

Exemplary Antibacterial Nanoparticles

Embodiments disclosed herein address one or more of the foregoing problems in the art of antibiotic compositions and/or treatments and can be implemented in various disclosed strategies for fighting infectious diseases and combatting antibiotic resistance. For example, disclosed embodiments include improved antimicrobial nanoparticle-based systems that structurally mimic the capsid structure and/or density distribution of protein turrets on the head of a bacteriophage and can act to primarily inhibit bacterial growth and, in some instances, ultimately kill pathogenic bacteria. A disclosed antibacterial nanoparticle (ANP) may include a silica core and a plurality of gold nanospheres conjugated to (or immobilized on) the silica core. At least some of the gold nanospheres can be coated with a layer of silver. Iron oxide nanospheres may also be conjugated to the silica core.

Such—and other—disclosed ANPs can provide individually potent antibacterial elements that are modularly assembled so as to accentuate the desired antibacterial properties of the individual components while beneficially minimizing their toxicity to eukaryotic tissue (e.g., within a patient or mammalian subject in need thereof or who is receiving prophylactic treatment). These ANPs can at least partially mimic the structure and/or dimensions of bacteriophages that infect only bacterial hosts using structure-based interactions with the appropriate nanofeatures on the bacterial membrane, cell wall, or other surface receptors.

The phage-mimicking ANPs disclosed herein may (a) selectively associate with bacterial membranes and, owing to the structural and chemical properties of the disclosed ANPs, disrupt cellular division and/or metabolic functions of the bacterial cell to cause stasis or death, (b) create a high surface area of antibacterial silver coating at silver concentrations that are lower than current antibacterial formulations—but which, within the context of the presently disclosed ANPs, are still providing antibacterial effects—(c) otherwise inhibit bacterial growth, (d) be non-toxic (and in some cases growth-promoting) to mammalian (e.g., human) cells, and (e) be quickly and modularly personalized on a case by case basis.

The ANPs of the present disclosure provide additional advantages, including the ability to be conjugated to other antimicrobial agents to increase their effectiveness in treating and/or reducing a likelihood of bacterial infections. For example, ANPs may be capped with antimicrobial peptides (AMPs), such as mutant chensinin-1-2, synthetic safencin-20, synthetic safencin-96, or AMPs disclosed herein. Additionally, or alternatively, ANPs may be conjugated to a polycationic polymer as a means of increasing bacterial association and antibacterial effectiveness of the associated ANPs.

Due to the adaptability and relative resilience of the disclosed ANPs, these particles can be combined with various medical products to treat or prevent (and/or reduce the likelihood of) bacterial infections. For example, ANPs disclosed herein may be added to a topological agent or disposed/coated on permanent implants, temporary implants, dental implants, surgical instruments, etc. to provide an antibacterial or disinfectant effect and/or to prevent the adhesion and/or growth of biofilms on associated implants/surgical instruments.

Those skilled in the art will recognize that the ANPs of the present disclosure provide additional benefits. For example, as with bacteriophages, the antibacterial properties of the presently disclosed ANPs are largely unaffected by genomically-acquired antibiotic resistance. Additionally, ANPs may be disposed on surfaces before bacterial colonization/infection can take place, thereby preventing (and/or reducing a likelihood of) pathogenic colonization and/or infection, in contrast to the reactive approach of administering broad-spectrum antibiotics after an infection is identified in a symptomatic patient. Accordingly, the use of ANPs, whether singly or in combination with other antimicrobials, may slow the increasing incidence of bacterial antibiotic resistance and may provide a viable alternative treatment (e.g., prescribed or prophylactic) for infectious diseases.

One additional advantage is that the ANPs of the present disclosure do not disrupt or mutate the DNA sequence of the antibiotic-resistant cassette in the infectious bacteria, as the mode of killing is through disruption of the bacterial membrane and not via DNA dimerization and fragmentation as in other techniques of incapacitating bacteria (e.g., radiation or heat killing). One beneficial effect of the disclosed ANPs preserving the antibiotic cassette sequence is that it allows for isolation of intact DNA from drug-resistant infections to determine how the pathogen has mutated using DNA sequencing. Such understanding of the various mutations can inform the design of treatment regimens and future therapies for combatting drug-resistant infections.

Attention is now directed to FIG. 1, which illustrates a conceptual representation of an ANP 120 of the present disclosure, as well as a conceptualization of a method for creating an ANP 120. As shown, an ANP includes a silica core 100. The silica core 100 may be synthesized, for example, by a sol-gel method such as the Stöber process involving hydrolysis and condensation of silica precursor tetraethyl orthosilicate ($Si(OEt)_4$, TEOS). The diameter of the resulting silica core 100 may be varied by varying the amount of ethanol, water, $NH_4OH$ solution, TEOS, and the material of the reaction vessel.

Although FIG. 1 indicates embodiments in which the silica core 100 has a diameter of approximately 45 nm or 130 nm, it will be appreciated that other diameters are within the scope of this disclosure. For example, a silica core 100 may have a diameter of 65 nm, 85 nm, 105 nm, or any diameter within a range, for example, of 12 nm to 800 nm, preferably between 20 nm to 200 nm.

In some instances, 45 nm silica cores 100 may be formed by combining and stirring 30 mL ethanol, 6 mL of deionized water, 1.125 mL TEOS, and 1.8 mL of 20% w/v $NH_4OH$ in water in a covered glass reactor for approximately eight hours or longer. In other instances, 130 nm silica cores 100 may be formed in a Teflon reactor by first stirring 5 mL ethanol with 1.3 mL TEOS and then adding a mix of 22 mL ethanol and 7 mL of 20% w/v $NH_4OH$ in water solution into the Teflon beaker, set to stir for approximately eight hours or longer at room temperature. For either desired silica core size, after stirring, the solutions may be centrifuged for approximately thirty minutes at room temperature to settle the synthesized nanoparticles and to separate them from the supernatant. The silica cores may then be washed, sonicated (e.g., for 20 seconds at 40% amplitude), and centrifuged with 10 mL ethanol twice.

FIG. 1 also illustrates that gold nanospheres 102 are conjugated to the silica cores 100 in an intermediate step to form an ANP 120. FIG. 1 depicts an embodiment in which the gold nanospheres have a diameter of approximately 5 nm, but other diameters are also usable. For example, gold nanospheres 102 may have a diameter within a range of 1.5 nm to 15 nm.

Gold nanospheres 102 may be formed, for example, by combining and stirring 40.4 mL deionized water, 400 µL NaOH (1M), 3 mL sodium citrate dihydrate (68 nM), and 1 mL THPC (85 mM) for approximately ten minutes at room temperature and then adding 2 mL gold chloride (25 mM) and then covering and stirring for another approximately eight hours or more.

The silica cores 100 may be prepared for adsorption by stirring for approximately eight hours or more with an additional 15 mL ethanol, 5 mL deionized water, and 1 mL APTES and then centrifuging the $SiO_2$-APTES cores for approximately thirty minutes at room temperature. The cores 100 may then be separated from the supernatant, and the amino-functionalized nanoparticle pellets may be washed, sonicated (e.g., for 20 seconds at 40% amplitude), and centrifuged with 10 mL ethanol twice at 9,000 rpm. The supernatant may then be discarded, and the residual pellets may be resuspended in 10 mL deionized water and sonicated (e.g., for 20 seconds at 40% amplitude).

Then, with a ratio of 1:2, for instance, the gold nanospheres solution may be mixed into the $SiO_2$-APTES cores solution and covered and stirred for approximately eight hours or more, resulting in gold nanospheres 102 conjugated to (or immobilized on) the silica cores 100 (referred to sometimes herein as $SiO_2$@Au). The $SiO_2$@Au nanoparticle solution may then be centrifuged at 9,000 rpm for approximately fifteen minutes at room temperature, followed by one or more washing-sonication, centrifugation cycles in, for example, 10 mL deionized water. It should be appreciated that the foregoing is an exemplary formulation and protocol for synthesizing silica cores and gold nanospheres.

In some instances, the gold nanospheres are conjugated to the silica core 100 so that the surface density of the gold nanospheres on the silica core 100 is similar to the surface density of protein turrets on bacteriophages. As an illustrative example, a 45 nm silica core 100 may include a 0.0077 $1/nm^2$ surface density of gold nanospheres, which is 88% similar to the surface density of protein turrets of the bacteriophage SpV4 (0.0068 $1/nm^2$). In other instances, the distance between the gold nanospheres disposed on the silica core 100 is such that the ratio of the silica core diameter to the distance between the gold nanospheres is within a range of 2 to 4. In other instances, the gold nanospheres are conjugated to the silica core 100 such that the ratio of the diameter of the silica core to the distance between the gold nanospheres is greater than 4. Additional discussion regarding the structural similarities between the ANPs and various bacteriophages is included hereinafter.

FIG. 1 also illustrates embodiments of ANPs having a silver coating 104 alloyed to the surface of the gold nanospheres 102 on the silica core 100. To accomplish this, in some instances, the $SiO_2$@Au nanoparticle solution is mixed with 10 mM $AgNO_3$ and 10 mM freshly prepared hydroquinone solution. Different proportions of $AgNO_3$ and hydroquinone solution may be utilized for alloying different concentrations of silver on the gold nanospheres 102. For example, a low concentration of silver (referred to herein as LS) may utilize 3 mL $AgNO_3$ and 337.5 µL hydroquinone solution, a medium concentration of silver (referred to herein as MS) may utilize 3 mL $AgNO_3$ and 1.8 mL hydroquinone solution, and a high concentration of silver (referred to herein as HS) may utilize 7.2 mL $AgNO_3$ and 5.76 mL hydroquinone solution.

Additional exemplary gold and silver concentrations for ANPs can include those detailed in Table 1 below.

TABLE 1

| ANPs | Gold concentration µg/ml (±SD) | Silver concentration µg/ml (±SD) |
|---|---|---|
| 45 nm LS | 637.61 (±52.91) | 17.64 (±9.77) |
| 130 nm LS | 679.59 (±51.04) | 26.62 (±13.57) |
| 45 nm MS | 624.86 (±39.65) | 92.15 (±58.60) |
| 130 nm MS | 652.48 (±67.73) | 141.63 (±81.42) |
| 45 nm HS | 665.21 (±66.93) | 123.25 (±87.91) |
| 130 nm HS | 635.32 (±50.35) | 189.22 (±122.13) |

After mixing the $SiO_2$@Au nanoparticle solution is mixed with a desired quantity of 10 mM $AgNO_3$ and 10 mM hydroquinone solution, in some instances, the mixed solution is covered completely with aluminum foil (e.g., to limit UV exposure) and stirred for approximately one hour. Then, the silver coating reaction may be stopped by centrifugation and discarding the supernatant. Various final concentrations of coated silver 104 are within the scope of this disclosure, depending on the size of the silica core 100, the gold nanospheres 102, and/or the intended concentration profile (e.g., LS, MS, HS). In some embodiments, the final silver coating 104 concentration ranges from 5 µg/mL to 350.5 µg/mL. Furthermore, it will be appreciated that, in some embodiments, less than all of the gold nanospheres 102 are coated with silver coating 104, whereas in other embodiments, all of the gold nanospheres 102 are coated with silver coating 104. In some implementations, coating fewer than all of the gold nanospheres 102 with silver coating 104 provides ANPs that are more easily implemented into antibacterial applications for use within the human body (e.g., orthopedic implants). By way of illustrative example, the United States Environmental Protection Agency (EPA) has established a chronic oral Reference Dose (RfD) of 5 µg/kg/day for silver, which broadly translates to 250 µg to 750 µg per person per day (depending on the weight of the person). At least some of the presently disclosed phage-mimicking ANPs include a maximum silver content of less than 200 µg (e.g., 189 µg/mL), with a predicted <1 µg/mL of silver ion leaching into solution, which is well below the EPA prescribed safety limit for silver exposure. Reducing the amount of silver coating 104 on gold nanospheres of the ANPs may provide even lower levels of silver.

The resulting $SiO_2$@Au@Ag nanoparticles 120 (ANPs) may then be washed and centrifuged (e.g., two additional times in 10 mL deionized water) and stored in darkness until intended use. As discussed hereinbelow, the ANPs 120 at least partially mimic the structure and/or dimensional characteristics of certain bacteriophages with icosahedral capsids (e.g., ΦX174) and exhibit unexpected antibacterial properties. After all, adhesion of bacteriophages to a host bacterium is not usually antibacterial. Most phages require a metabolically active host to replicate their genomic nucleic acid and to form new virions. Thus, the infection following adhesion and the replication of phages within the bacterial host is typically the mode of bactericidal activity exhibited by phages.

Figure 2:
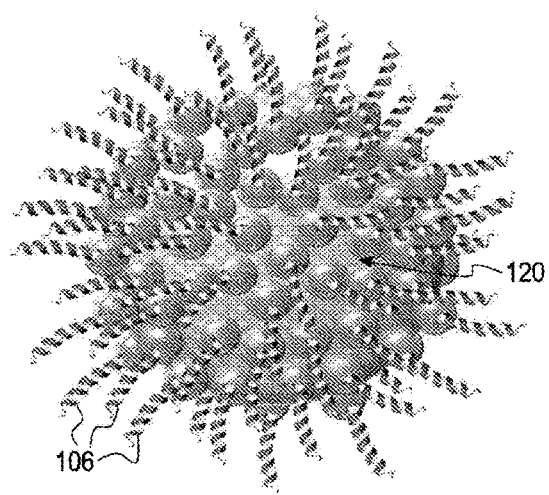
FIG. 2 illustrates a conceptual representation of antibacterial peptides conjugated to the silver-coated gold nanospheres of an antibacterial nanoparticle of the present disclosure.
Figure 3:
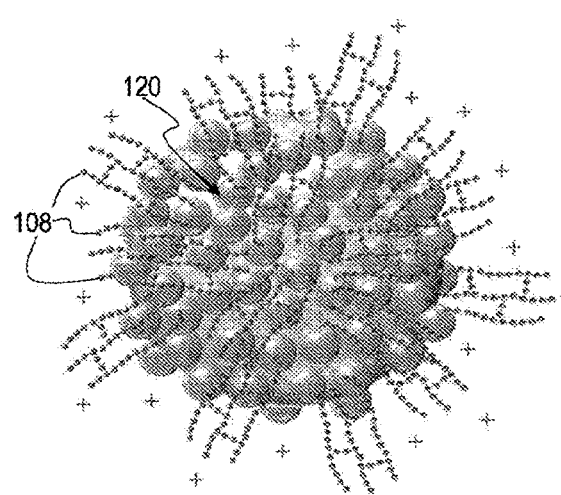
FIG. 3 illustrates a conceptual representation of polycationic polymers conjugated to the silver-coated gold nanospheres of an antibacterial nanoparticle of the present disclosure.
Figure 4:
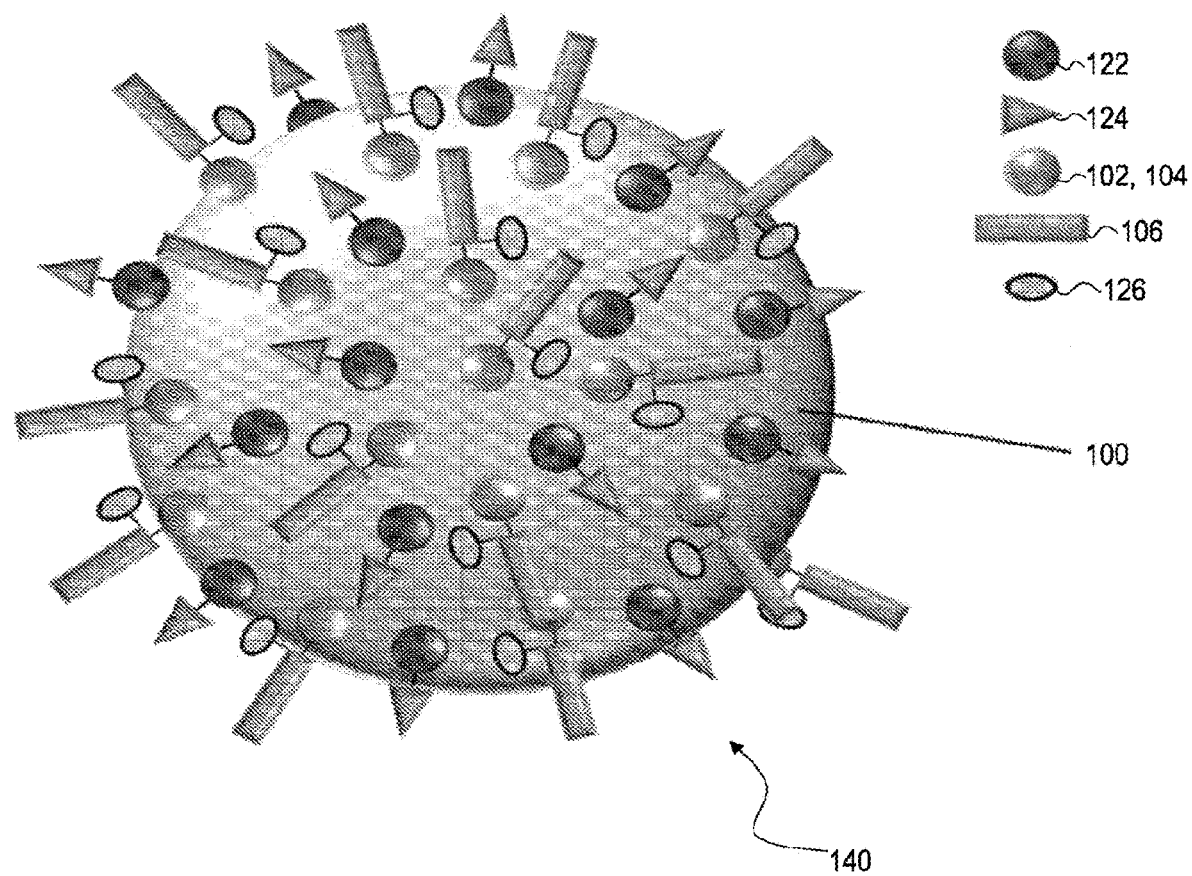
FIG. 4 illustrates a conceptual representation of a modular ANP with iron oxide nanospheres, cell penetrating peptides, silver-alloyed gold nanospheres, antimicrobial peptides, and fluorescein molecules modularly anchored thereto.

In addition to silver-coated gold nanospheres, FIG. 2-4 illustrate that an ANP 120 may include additional modularly attached additives to accomplish or customize antibacterial activity or other properties of the ANPs. For example, FIG. 2 illustrates an ANP 120 with a plurality of antimicrobial peptides 106 (AMPs) conjugated thereto (referred to sometimes herein as ANP@AMP). Naturally occurring AMPs often have broad and numerous bacterial targets and are used by many organisms to control bacterial populations or to compete within their environments. Synthetic AMPs may mimic naturally occurring AMPs and may be more easily produced for medicinal applications and may also beneficially be less prone to bacterial resistance than alternative antibiotic moieties. AMPs 106 may be attached to the ANPs 120, for example, by a linking group (e.g., a silane or a thiol group).

It should be noted that a plurality of different AMPs 106 may be conjugated to an ANP 120 of the present disclosure. In some embodiments, the peptides contain only amino acids. That is, in some instances, the peptides are not post-translationally modified. It should be appreciated, therefore, that the synthetic AMPs may include peptides containing unmodified amino acids and are not lipopeptides or any other form of peptide that is modified with another class of organic molecule. For example, an ANP may be conjugated to one or more synthetic antimicrobial peptides disclosed in Table 2 below.

TABLE 2

| AMP Name | Amino Acid Sequence | SEQ ID NO |
|---|---|---|
| Mutant chensinin-1-2 | SAVWRWRRFWLRKRK | SEQ ID NO: 1 |
| Safencin-20 | AWKKTIRQYLKNKIKKKGRKAVIAW | SEQ ID NO: 2 |
| Safencin-96 | AWKEKIRKKLKNEIKKKWRKAVIAW | SEQ ID NO: 3 |
| Safencin | AGKETIRQYLKNEIKKKGRKAVIAW | SEQ ID NO: 4 |
| Peptide 20 | AWKKTIRQYLKNKIKKKGRKAVIAW | SEQ ID NO: 5 |
| Peptide 52 | AGKKTIRQYLKNKIKKKWRKAVIAW | SEQ ID NO: 6 |
| Peptide 60 | AGKKTIRQYLKNKIKKKGRKWVIAW | SEQ ID NO: 7 |
| Peptide 90 | AWKKTIRQYLKNEIKKKWRKAVIAW | SEQ ID NO: 8 |
| Peptide 91 | AWKETIRQYLKNKIKKKWRKAVIAW | SEQ ID NO: 9 |
| Peptide 92 | AWKKTIRQYLKNKIKKKWRKAVIAW | SEQ ID NO: 10 |
| Peptide 93 | AWKEKIRQYLKNEIKKKWRKAVIAW | SEQ ID NO: 11 |
| Peptide 94 | AWKETIRKYLKNEIKKKWRKAVIAW | SEQ ID NO: 12 |
| Peptide 96 | AWKEKIRKKLKNEIKKKWRKAVIAW | SEQ ID NO: 13 |

It will be appreciated that the foregoing list of AMPs 106 is exemplary only and non-limiting. As will be discussed hereinafter, in some instances, conjugating one or more AMPs 106 with ANPs 120 improves the antibacterial effectiveness of the ANPs 120.

In addition to, or as an alternative to, AMPs 106, FIG. 3 shows a plurality of standard model polycationic polymers 108 conjugated to an ANP 120. The polymers 108 impart a net positive charge on the ANP 120, and conjugating one or more polycationic polymers 108 with ANPs 120 may affect the antibacterial effectiveness of the ANPs 120 (e.g., when immobilized on an implant-grade metal surface).

Polycationic polymers can be conjugated to ANPs by any method known in the art. By way of example and not limitation, polycationic polymers can be conjugated to ANPs via chemisorption of thiol to the Au/Ag or noble metal surface. The thiol group can be introduced by incorporating cysteine as an end amino acid in the peptide sequences. For polycationic polymers, a thiol derived acid group (e.g., 11-mercaptoundecanoic acid or 3-mercaptosuccinic acid) can be linked to linear polycationic polymers such as linear Polyethyleneimine in, for example, a 1:1 ratio. The amine group can then be covalently linked to the acid group by employing carbodiimide/N-hydroxy succinimide chemistry (EDC/NHS). The resultant thiol derivatized polycationic polymer can then be immobilized onto the ANPs by means of chemisorption of the thiol on the Au/Ag nanospheres.

Additionally, or alternatively, other nanospheres may be directly fused to the surface of the silica core 100. For example, FIG. 4 illustrates a conceptual representation of a modular ANP 140 with iron oxide nanospheres 122, cell penetrating peptides (CPPs) 124, silver-alloyed gold nanospheres (102, 104), AMPs 106, and fluorescein molecules

126 modularly anchored thereto. In some instances, iron oxide nanospheres ($Fe_3O_4$) 122 are conjugated to the silica core 100 by being directly fused thereto or by being linked to the amine groups on the silica core using carbodiimide chemistry. The diameter of the iron oxide nanospheres 122, in some embodiments, is within a range of 3 nm to 10 nm, and the iron oxide nanospheres 122 may be, in some instances, conjugated to AMPs 106 described above.

In some instances, as shown in FIG. 4, the iron oxide nanospheres 122 are interspersed in between the discontinuous shell of silver-alloyed gold nanospheres (102, 104) of the silica core 100 to generate a magnetic hyperthermia inducing shell around the silica core 100, which may physically disrupt the bacterial cells by inducing localized magnetic hyperthermia on the modular ANPs 140 through an externally applied magnetic AC field, thereby limiting the possible recurrence of infection. Furthermore, in some embodiments, silane-modified cell-penetrating peptides (CPPs) 124 for penetrating eukaryotic cells are immobilized on the iron oxide nanospheres through silanization to target intracellular bacterial pools that are often the main reason for recurring infections (e.g., urinary tract infections caused by Extraintestinal Pathogenic *Escherichia coli*).

Additionally, in some implementations, modular ANPs 140 include fluorescein reporter molecules 126 anchored in between the AMPs 106 on the surface of the silver-alloyed gold nanospheres 102, 104. The fluorescein reporter molecules 126 may be anchored by a cephalosporin linker or a thiol linker, as shown in FIG. 4. When in close proximity to the silver-alloyed gold nanospheres 102, 104, the fluorescein reporter molecules are blacked out because of metal quenching. The fluorescein molecules 126 may, in some instances, become dissociated from the modular ANPs 140 by enzymes (e.g., β-lactamase) secreted by infectious bacteria, and therefore avoid metal quenching and become detectable by fluorescence detection methods to indicate the presence of a bacterial infection.

Accordingly, an ANP 120 of the present disclosure may be modularly outfitted with various components (e.g., antimicrobial/antibacterial peptides, polycationic polymers, iron oxide nanospheres, cell-penetrating peptides, fluorescein molecules, etc.) according to the desired therapeutic treatment or purpose. In some instances, a modular ANP 140 may provide an antibiotic-independent platform that can treat persistent infection, prevent (and/or reduce a likelihood of) recurrent infection, and/or promote complete long-term recovery.

Figure 5A:
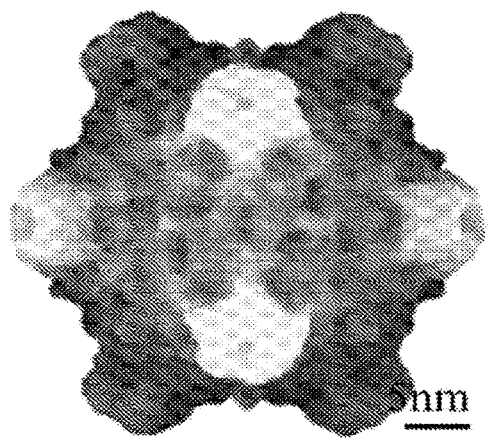
FIG. 5A illustrates a surface rendering of procapsid particles of bacteriophage Φ174 obtained by cryo-electron microscopy data.
Figure 5B:
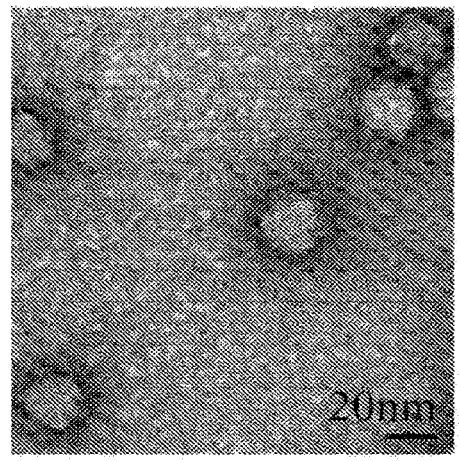
FIG. 5B is a cryo-high-resolution transmission electron microscopy (cryo-HRTEM) image of procapsid particles of bacteriophage ΦX174.
Figure 5C:
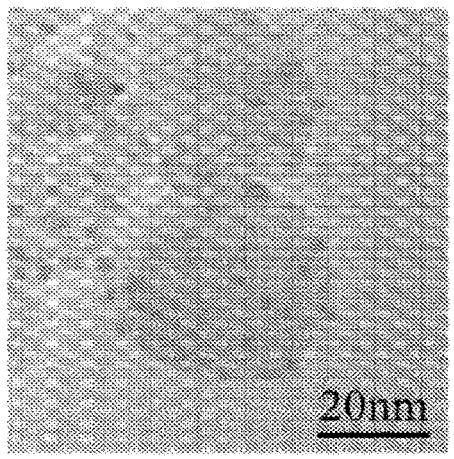
FIG. 5C is an HRTEM image of 45 nm $SiO_2$@Au@Ag antibacterial nanoparticles with high silver coating on the gold nanospheres.
Figure 5D:
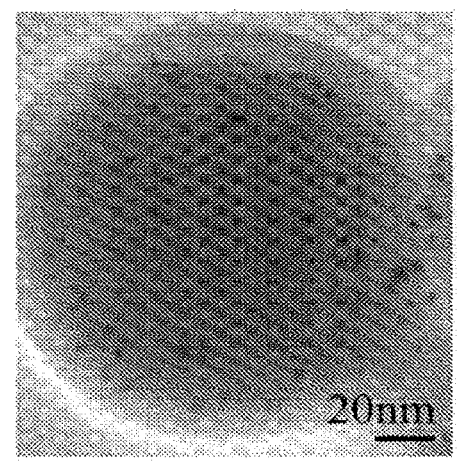
FIG. 5D is an HRTEM image of 130 nm $SiO_2$@Au@Ag antibacterial nanoparticles with high silver coating on the gold nanospheres.
Figure 5E:
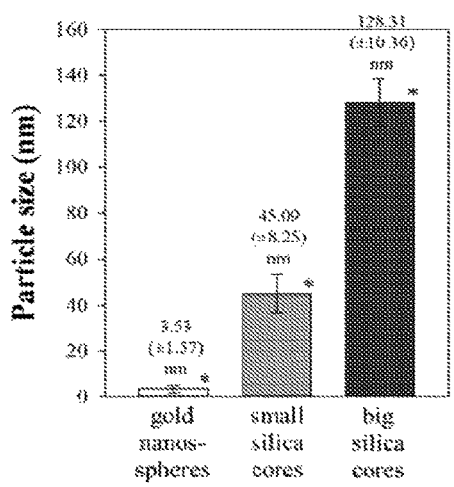
FIG. 5E is a graphical representation of the average diameter of the gold nanospheres, the 45 nm $SiO_2$ cores, and the 130 nm $SiO_2$ cores.
Figure 5F:
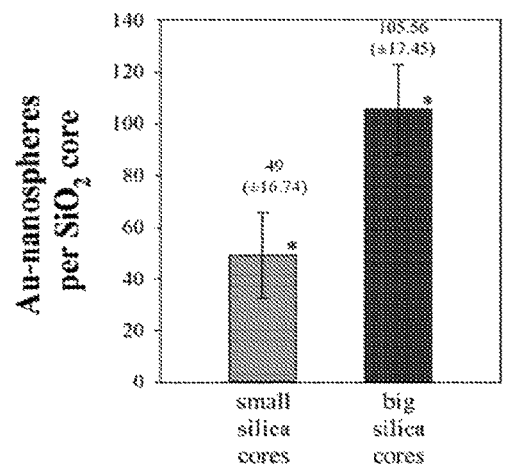
FIG. 5F is a graphical representation of the amount of gold nanospheres that were counted on both silica core sizes.

FIG. 5A-5F illustrate a surface rendering of procapsid particles of bacteriophage ΦX174 (FIG. 5A), a high-resolution transmission electron microscopy (HRTEM) image procapsid particles of bacteriophage ΦX174 (FIG. 5B), an HRTEM image of 45 nm SiO-2@Au@Ag ANPs with high silver coating on the gold nanospheres (FIG. 5C), an HRTEM image of 130 nm $SiO_2$@Au@Ag antibacterial nanoparticles with high silver coating on the gold nanospheres (FIG. 5D), a graphical representation of the average diameter of the gold nanospheres, the 45 nm $SiO_2$ cores, and the 130 nm $SiO_2$ cores (FIG. 5E), and a graphical representation of the amount of gold nanospheres that were counted on exemplary ANPs with 45 nm and 130 nm silica core sizes (FIG. 5F).

Ninety-seven percent of bacteriophages infecting ESKAPE organisms belong to Caudovirales, an order of tailed bacteriophages with icosahedral capsids (45-170 nm). At least some of the ANPs of the present disclosure target the evolutionarily constant bacterial cell wall/membrane with high specificity by structurally mimicking the capsid architecture and/or function of phages that target only bacterial cells. At least some ANPs include a silica core studded with smaller, silver coated gold nanospheres on their surface, recreating the high surface area and 'bubble-wrap' structure of icosahedral capsids (e.g., ΦX174, as shown in to FIG. 5, A, B).

The production of phage-mimicking ANPs disclosed herein (e.g., $SiO_2$@Ag@Au, without any attached AMPs, polymers, etc.) was investigated by Transmission Electron Microscopy (TEM). FIG. 5C shows TEM images of 45 nm silica core and FIG. 5D shows TEM images of 130 nm silica core ANPs with HS. TEM image analysis, represented in FIG. 5E, reveals that the small and large $SiO_2$ cores had diameters of approximately 45 nm (±8.25 nm) and 130 nm (±10.36 nm), respectively, and were covered with 3.5 nm (±1.57 nm) gold-nanospheres. Additionally, FIG. 5F shows that the number of gold nanospheres was approximately 50 for the 45 nm silica core size and approximately 105 for the 130 nm silica core size.

In general, as compared with various tailed bacteriophages (e.g., P68, phi812, φKZ) and tailless bacteriophages (e.g., ΦX174, PM2, PRD1, STIV, SpV4) the size of smaller ANPs (e.g., 45 nm) relates better to the capsid sizes of tailless bacteriophages than larger (e.g., 130 nm) ANPs. Both 45 nm and 130 nm cores sizes carry more gold nanospheres per unit area in comparison to the number of protein turrets on the heads of the bacteriophage's capsids (e.g., approximately 4 times and 8 times higher, respectively). Regardless, the interspacing between the gold nanospheres of small ANPs (e.g., 2.02 nm for 45 nm ANPs) is much smaller than the geometrically consistent distance between the protein-turrets covering the surface of the phage capsids. On the other hand, the gold nanospheres interspaced on larger ANPs (e.g., 9.87 nm for 130 nm ANPs) is comparable to the protein turret interspacing found on smaller bacteriophages (e.g., P68, ΦX174, and SpV4, with interspacing 11.33 nm, 8.28 nm, and 9.31 nm, respectively).

Interestingly, the bacteriophage SpV4 possesses a surface density of protein turrets (0.0068 l/$nm^2$) that is 88% similar to the surface density of gold nanospheres (0.0077 l/$nm^2$) on small (45 nm) ANPs. The SpV4 bacteriophage belongs to the viral family of Microviridae which are small (25-27 nm), tailless bacteriophages with icosahedral capsids. The genus of SpV4 is a close match to the family of Chlamydiaphages, which, as the name suggests, are known to infect various species of the obligate intracellular and pathogenic *chlamydia*. The Chlamydiaphages are known to initiate infection with the bacterial host cell by pilus adsorption which is dependent on the shape and structure of the phage. Additionally, the surface density of protein turrets on the *S. aureus* infecting bacteriophage P68 (0.0023 l/$nm^2$) is 85% similar to the surface density of gold nanospheres on the larger (130 nm) ANPs (0.0020 l/$nm^2$). Thus, the surface density of silver-coated gold nanospheres on the silica cores of both 45 nm and 130 nm ANPs sizes is closely related to the surface density of protein turrets of pathogen-infecting bacteriophages which is indicative of the phage structure mimicking properties of at least some of the disclosed ANPs (e.g., $SiO_2$@Ag@Au).

For reference, Table 2 below shows structural comparisons of the heads of tailed (P68, phi8812, φKZ) and tailless bacteriophages (ΦX174, PM2, PRD1, STIV, SpV4) with small (45 nm) and large (130 nm) phage-mimicking ANPs with respect to number of protein turrets per capsid (number gold nanospheres per silica core), capsid diameter (silica core diameter), interspacing between protein turrets on capsid (interspacing between gold nanospheres on silica core), surface area of the capsid (surface area silica core), and surface density of protein turrets (surface density of gold nanospheres).

TABLE 2

| Tailed bacteriophage | Number of protein turrets/ capsid | Capsid diameter (nm) | Interspacing between protein turrets on capsid (nm) | Surface area of capsid ($nm^2$) | Surface density of protein turrets ($1/nm^2$) |
|---|---|---|---|---|---|
| P68 | 12 | 48 | 11.33 | 5191 | 0.0023 |
| phi812 | 12 | 90 | 29.58 | 24916 | 0.0005 |
| φKZ | 12 | 145 | 59.80 | 46407 | 0.0003 |

| Tailless bacteriophage | Number of protein turrets/ capsid | Capsid diameter (nm) | Interspacing between protein turrets on capsid (nm) | Surface area of capsid ($nm^2$) | Surface density of protein turrets ($1/nm^2$) |
|---|---|---|---|---|---|
| ΦX174 | 12 | 28 | 8.28 | 3068 | 0.0039 |
| PM2 | 12 | 59 | 28.61 | 10120 | 0.0012 |
| PRD1 | 12 | 64 | 17.32 | 11898 | 0.0010 |
| STIV | 12 | 70 | 27.25 | 14496 | 0.0008 |
| SH1 | 12 | 82 | 36.44 | 15827 | 0.0008 |
| SpV4 | 18 | 31 | 9.31 | 2635 | 0.0068 |

| phage-mimicking ANPs | Number of Au nano-spheres/ silica core | Silica core diameter (nm) | Interspacing between Au nanospheres on silica core (nm) | Surface area of silica core ($nm^2$) | Surface density of Au Nano-spheres ($1/nm^2$) |
|---|---|---|---|---|---|
| small (45 nm) | 49 | 45 | 2.02 | 6362 | 0.0077 |
| large (130 nm) | 106 | 130 | 9.87 | 53093 | 0.0020 |

Furthermore, although there is a broad range of values for the interspacing of protein turrets on bacteriophages (e.g., approximately 8 nm to 29 nm for ΦX174, PM2, PRD1, STIV, SpV4), the range of ratios of the capsid diameter to the interspacing of the spikes on various bacteriophage capsids appears to be much more compact (e.g., approximately 2 to 3.9 for ΦX174, PM2, PRD1, STIV, SpV4). For at least some ANPs disclosed herein, the ratio of the silica core nanoparticle diameter to the interspacing of the mini Au—Ag nanospheres on the core is 10.8 for a 45 nm core and 13 for a 130 nm core. Even though the ratio of the core nanoparticle diameter to the interspacing of mini Au—Ag nanospheres on a core may be different from the to ratio of the capsid diameter to the interspacing of the spikes on the bacteriophage capsids, the ANPs with AMPs capped on their surface exhibited broad-spectrum bactericidal activity (as discussed hereinbelow).

For example, PRD1 is a phage that attacks a broad swathe of Gram-negative bacteria. The ratio of PRD1 capsid diameter to protein turret interspacing is approximately 2.6. The ratio of the core diameter of an exemplary 45 nm silica core ANP to the interspacing of the mini Au—Ag nanospheres on the silica core was approximately 4× higher than the ratio of the PRD1 capsid diameter to protein turret interspacing. The ratio was 5× higher than PRD1's ratio for an exemplary 130 nm silica core ANPs. This indicates that, in at least some instances, phage mimicking structures (e.g., ANPs) do not have to be exact replicates of the natural bacteriophages, so long as the structural characteristics of interspaced protein turrets/spikes are mimicked by the ANPs. As discussed herein, the structure-function relationship seen in bacteriophages can be replicated synthetically using, for example, peptide capped Au—Ag mini nanospheres on ANPs with peptide spacing ratios that result in ratios of the core nanoparticle diameter to the interspacing of mini Au—Ag Nanospheres on the core that are whole integer multiples (within a 10%±deviation) of the ratio of the capsid diameter to the interspacing of the protein turrets/spikes on the bacteriophage capsids.

FIG. 6A-6D illustrates cell viability (represented as a % relative to a control) using various nanoparticles: $SiO_2$, $SiO_2@Au$, $SiO_2@Au@Ag$ with low silver coating (LS), $SiO_2@Au@Ag$ with medium silver coating (MS), $SiO_2@Au@Ag$ with high silver coating (HS) at both low concentration (LC) and high concentration (HC) and for various $SiO_2$ core sizes (65 nm and 130 nm). For the cytotoxicity data represented in FIG. 6A-6D, HaCaT human epithelial keratinocytes were used, maintained in Dulbecco's Modified Eagle's Medium (DMEM) with 10% heat-inactivated fetal bovine serum (FBS), and incubated at 37° C. with 5% $CO_2$ in 100 mm culture dishes. The ethidium homodimer cell death assay was used to determine the cytotoxicity of all five synthesized nanoparticle variations ($SiO_2$, $SiO_2@Au$, $SiO_2@Au@Ag$ LS (low silver), $SiO_2@Au@Ag$ MS (medium silver), and $SiO_2@Au@Ag$ HS (high silver). For this assay, HaCaT cells were grown to approximately 80% confluency in 24 well tissue culture plates with DMEM. Before the nanoparticle treatment, DMEM was aspirated from the wells, and the cells were washed with PBS. Then PBS was aspirated from the wells, and the nanoparticle solution (in DMEM) was added in two concentrations. The ratio of nanoparticles per HaCaT cell used in this assay was adapted to the ratio of nanoparticles per bacterial cells used in the biocidal activity assays. "LC" (low concentration) is approximately $6.99 \times 10^{11}$ particles/mL for the 65 nm ANP@AMPs and $1.09 \times 10^{11}$ particles/mL for the 130 nm ANP@AMPs. The high concentration (HC) was approximately $1.40 \times 10^{12}$ particles/mL for the 65 nm ANP@ANPs and $2.19 \times 10^{11}$ particles/mL for the 130 nm ANP@ANPs. Cells were then incubated for 16 hours at 37° C. with 5% CO2. After incubation, the DMEM medium was aspirated, and cells were washed with PBS to remove the majority of the nanoparticles. 4 µM ethidium homodimer in PBS was added, and cells were incubated for 30 minutes. The level of fluorescence was determined using a plate reader set to 528 nm excitation and 617 nm emission with a cut-off value of 590 nm. The percentage of dead cells was determined by adding 0.1% (w/v) Saponin (Sigma) to each well following the initial reading and allowing the plate to incubate for an additional 20 minutes at room temperature and shaking before reading the plate a second time at the same settings. Percent membrane permeabilization was calculated by dividing the fluorescence values with intact cells by the fluorescence values after cell disruption by saponification. Each treatment condition was performed in triplicate at least, the average as % cell viability (relative to the control) plus standard deviation of all condition was plotted together for comparison. Significance was determined by ANOVA and t-test (one tail and two tail).

Figure 6A:
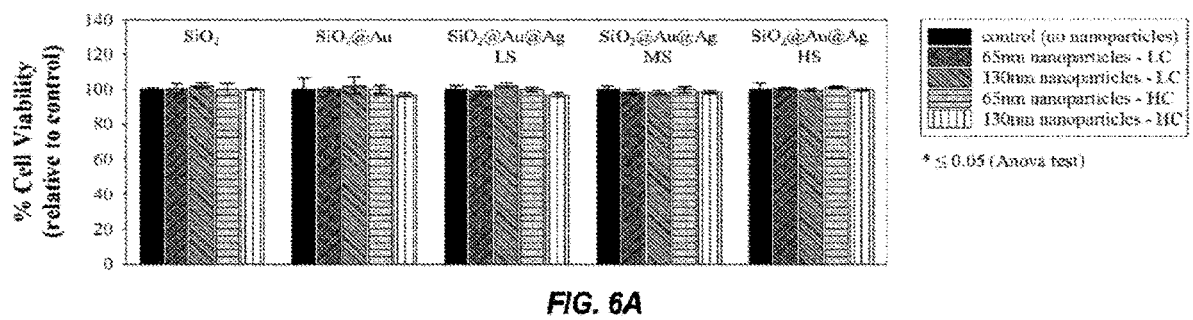
FIG. 6A-6D illustrates cell viability (represented as a % relative to a control).

As shown in FIG. 6A, all five synthesized nanoparticle variations ($SiO_2$, $SiO_2@Au$, $SiO_2@Au@Ag$ LS, $SiO_2@Au@Ag$ MS, and $SiO_2@Au@Ag$ HS are highly biocompatible with human skin cells (e.g., HaCaT). Sub-samples of the HaCaT left in incubation with the nanoparticles for approximately 12 h showed growth and a healthy appearance of the cells. The LC of Ag nanoparticles ≤10 nm (1180±140 µg/mL) against eukaryotic fibroblasts cells is lower than that of Ag nanoparticles >10 nm (1760±110 µg/mL) since the smaller Ag nanoparticles are easily taken up by cells and concentrated intracellularly, much more than the >10 nm Ag nanoparticles. The lack of abundance of cysteine residues on eukaryotic cell membranes combined with the size of the eukaryotic cells being ~200 fold larger than the nanoparticles and the multiple points of simultaneous contact between the negatively charged Au/Ag nanospheres with the negatively charged cell membrane appears to increase the repulsion of the ANPs from the surface of eukaryotic cells. The arrangement of the sub-5 nm Au/Ag nanospheres on a >45 nm silica core may also ensure that the Au/Ag nanospheres do not present themselves as <5 nm Ag nanoparticles, thereby reducing the probability of the ANPs from permeabilizing the eukaryotic cell membrane and increasing the biocompatibility of the ANPs towards eukaryotic cells.

Figure 6B:
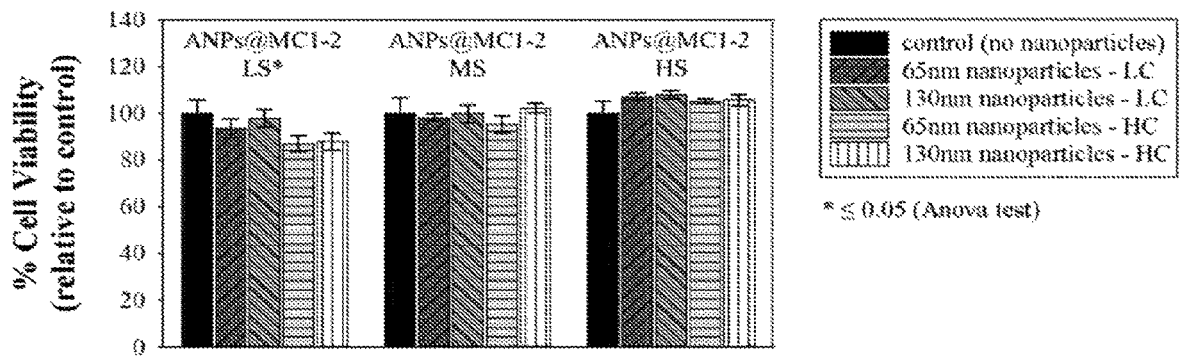
Figure 6C:
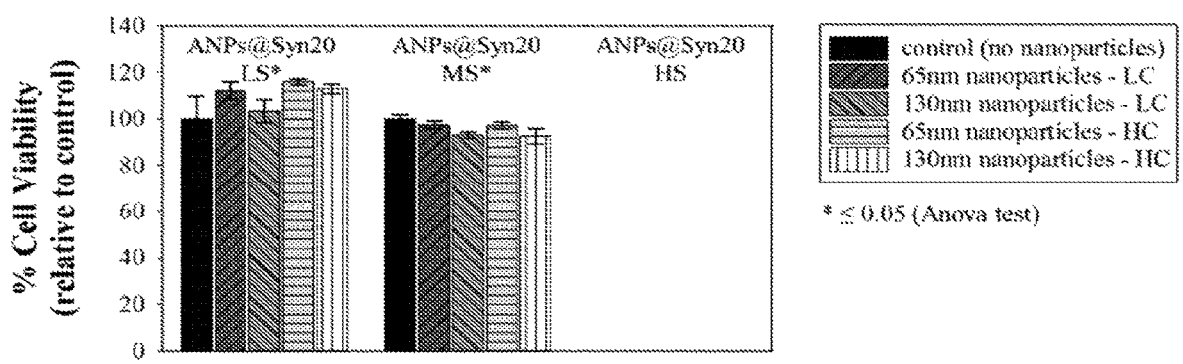
Figure 6D:
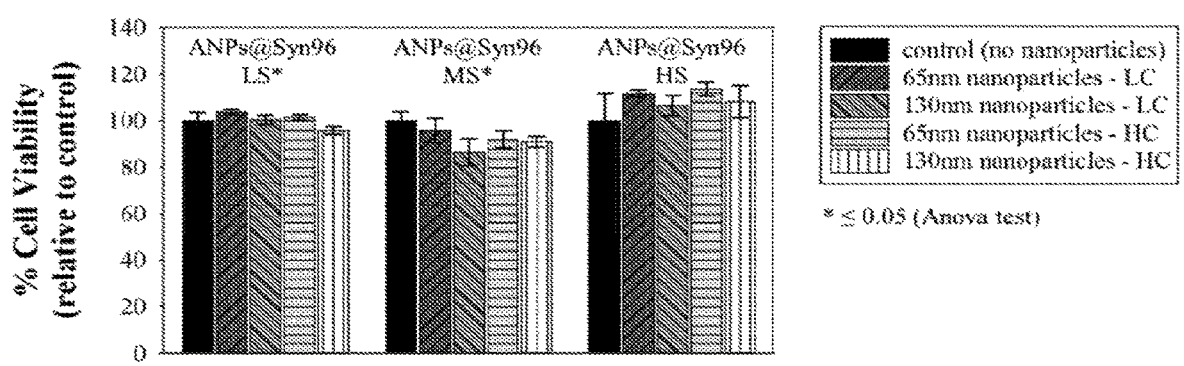

FIG. 6B-D illustrate cell viability (represented as a % relative to a control) during treatment with antibacterial nanoparticles (ANPs), $SiO_2$@Au@Ag, of various $SiO_2$ core sizes conjugated to the antimicrobial peptide (AMP) mutant chensinin-1-2 (MC1-2) with various silver coating thicknesses (LS, MS, HS) and at various concentrations (LC, HC, C), ANPs, $SiO_2$@Au@Ag, of various $SiO_2$ core sizes conjugated to synthetic safencin-20 (Syn20) with various silver coating thicknesses (LS, MS, HS) and at various concentrations (LC, HC, and D), and ANPs, $SiO_2$@Au@Ag, of various $SiO_2$ core sizes conjugated to synthetic safencin-96 (Syn96) with various silver coating thicknesses (LS, MS, HS) and at various concentrations (LC, HC). As is evident in FIGS. 6B, 6C, and 6D, many of the ANPs@AMPs are not significantly cytotoxic and therefore may be used in medical applications, such as topological applications, medical implants, surgical instruments, etc.

Examples of Antibacterial Activity of ANPs

S. aureus strain USA300 is a methicillin-resistant (MRSA) strain predominantly associated with skin and soft tissue infections, although it has also been recovered from severe cases of invasive disease including bacteremia, endocarditis, necrotizing pneumonia, and osteomyelitis. FIG. 7A-7F illustrate the growth of S. aureus USA300 with various concentrations of ANPs, including 45 nm ($SiO_2$ core diameter) $SiO_2$@Au@Ag (ANPs) with LS (FIG. 7A), 45 nm ANPs with MS (FIG. 7B), 45 nm ANPs with HS (FIG. 7C), 130 nm ANPs with LS (FIG. 7D), 130 nm ANPs with MS (FIG. 7E), and 130 nm ANPs with HS (FIG. 7F). FIG. 7A-7F indicate that with increasing silver coating, the ANPs slow down the growth of the microorganism more and more as well and suppress the optical density (OD)—a surrogate for monitoring bacterial growth within in vitro broth culture, as known in the art—from reaching the maximum (possibly lower) cell count. The highest silver concentration used in the experiment represented in FIG. 7A-7F was approximately 95 µg/mL (on 130 nm ANPs HS; considering the dilution factor), which was quite effective in inhibiting the growth of S. aureus USA300.

It should be appreciated that the OD measurement is a surrogate for cell number within a broth culture. Because OD is essentially the measurement of the turbidity of the sample, additional bacterial cells in the solution cause an increase in the OD reading. Thus, if a culture is inoculated with a relatively low abundance of bacteria, any growth thereof can be observed by monitoring the optical density of the sample. However, an increase in the OD measurement of a culture is not necessarily congruous with an increase in the number of viable cells within that culture, as a metabolically inactive cell refracts light—and consequently affects the OD measurement of a broth culture-similar to a metabolically active cell. Further, OD measurements for monitoring growth characteristics of a bacterial population in response to a stress are typically performed in a fixed volume of liquid culture. This allows for the three basic phases of bacterial growth to be observed (i.e., lag phase, exponential growth phase, and stationary phase) and compared. For example, an increased lag phase and/or delayed onset of exponential growth can indicate an immediate stress upon the inoculum. A slower exponential phase can similarly indicate a stress on the dividing culture (e.g., replication time is increased and/or death rate is increased). Also, if the volume is constant, the toxic byproducts of cellular division and/or limited resources can cause a predictable onset of (or the predictable transition from exponential growth to) stationary phase, leading to an expected maximum OD for the given bacterium in the provided culture conditions. Any decrease to the expected maximum OD can correspond with, for example, an underutilization of resources (i.e., a metabolic deficiency), a sensitivity to metabolic byproducts (i.e., a structural or metabolic deficiency), and/or an expenditure of the available resources amounting to a lower number of cells (or morphologically smaller cells)—which can occur as a result of an increased killing of cells within the media. Accordingly, one having skill in the art recognizes that the OD measurement, while having some flaws, is a useful tool for measuring the effects of various stresses and/or potential antibacterial compositions-particularly when compared to non-stressed, control cultures.

Figures 7A, 7B, 7C:
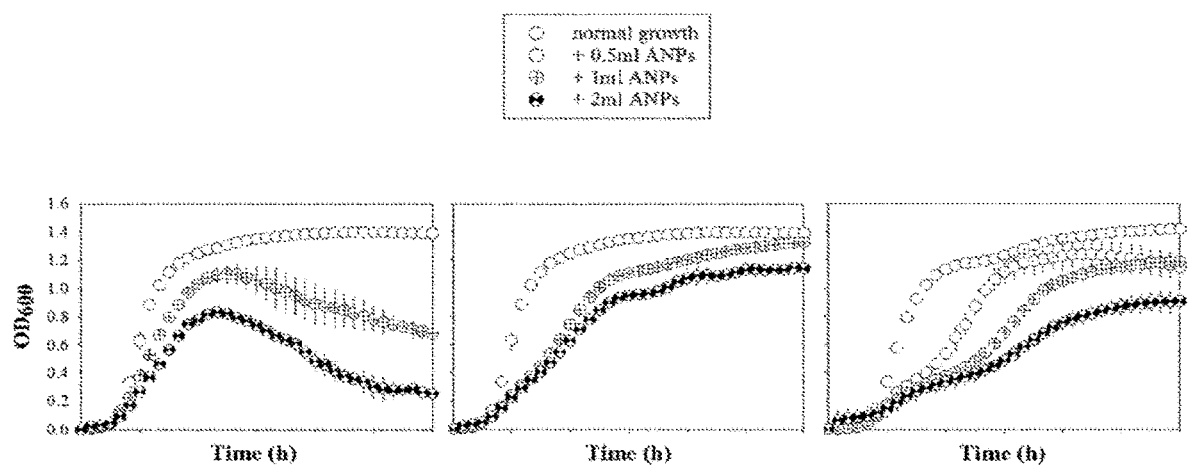
FIG. 7A-7F illustrates the growth of *Staphylococcus aureus* USA300 with various concentrations and types of nanoparticles, including 45 nm ($SiO_2$ core diameter) $SiO_2$@Au@Ag (ANPs) with LS (FIG. 7A); 45 nm ANPs with MS (FIG. 7B); 45 nm ANPs with HS (FIG. 7C); 130 nm ANPs with LS (FIG. 7D); 130 nm ANPs with MS (FIG. 7E); and 130 nm ANPs with HS (FIG. 7F)
Figures 7D, 7E, 7F:
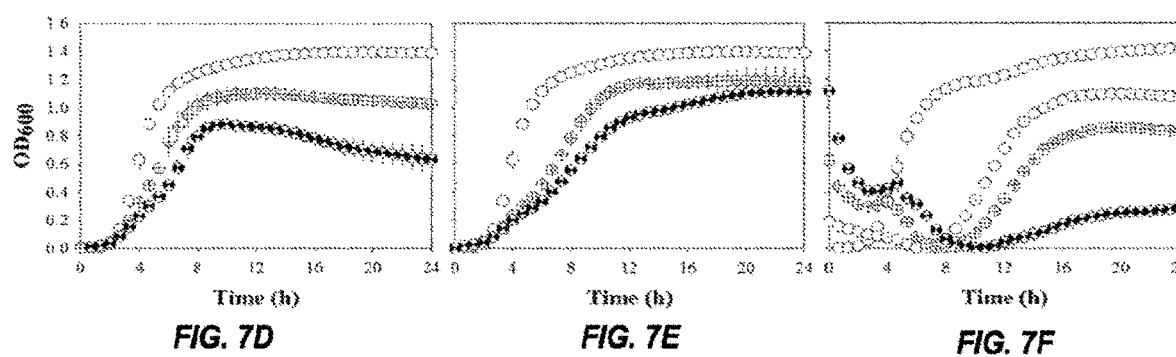

FIG. 7A shows that a 1 mL solution of 45 nm $SiO_2$@Au@Ag (ANPs) with low silver caused the S. aureus USA 300 culture to reach only 79% of the maximum expected OD and that a 2 mL ANPs solution caused the associated S. aureus USA300 culture to reach only 60% of the maximum expected OD (when compared with control). FIG. 7B shows that a 1 mL solution of 45 nm ANPs with medium silver caused slower growth with the S. aureus USA300 culture reaching 95% of the maximum expected OD and that a 2 mL ANPs solution caused slower growth with the S. aureus USA300 culture reaching 82% of the maximum expected OD. FIG. 7C shows that a 0.5 mL solution of 45 nm ANPs with high silver caused slower growth with the S. aureus USA300 culture reaching 87% of the maximum expected OD, that a 1 mL ANPs solution caused slower growth with the S. aureus USA300 culture reaching 83% of the maximum expected OD, and that a 2 mL ANPs solution caused slower growth with the S. aureus USA300 culture reaching 64% of the maximum OD. FIG. 7D shows that a 1 mL solution of 130 nm ANPs with low silver caused the associated S. aureus USA300 culture to reach only 79% of the maximum expected OD and that a 2 mL ANPs solution caused the associated S. aureus USA300 culture to reach only 63% of the maximum expected OD. FIG. 7E shows that a 1 mL solution of 130 nm ANPs with medium silver caused slower growth with the S. aureus USA300 culture reaching 85% of the maximum expected OD and that a 2 mL ANPs solution caused slower growth with the S. aureus USA300 culture reaching 80% of the maximum expected OD. FIG. 7F shows that a 0.5 mL solution of 130 nm ANPs with high silver delayed the onset of the exponential growth phase (approximately 4.7 h) and resulted in slower growth with the S. aureus USA300 culture reaching 77% of the maximum expected OD, that a 1 mL ANPs solution delayed the onset of the exponential growth phase (approximately 6.2 h) and resulted in slower growth with the S. aureus USA300 culture reaching 60% of the maximum expected OD, and that a 2 mL ANPs solution delayed onset of the exponential growth phase (approximately 8.4 h) and resulted in slower growth with the *S. aureus* USA300 culture reaching 21% of the maximum expected OD.

The antibacterial efficacy of the SiO$_2$@Au@Ag ANPs was then tested on 3 other species of bacteria: *Corynebacterium striatum*, *Pseudomonas aeruginosa* FRD1, and *Enterococcus faecalis*. Together with *S. aureus*, these four species are often regarded as opportunistic nosocomial pathogens and represent a high risk for immunocompromised patients in the clinical environment in addition to a cohort of bacteria that are commonly associated with increased antibiotic resistance.

Figures 8A, 8B:
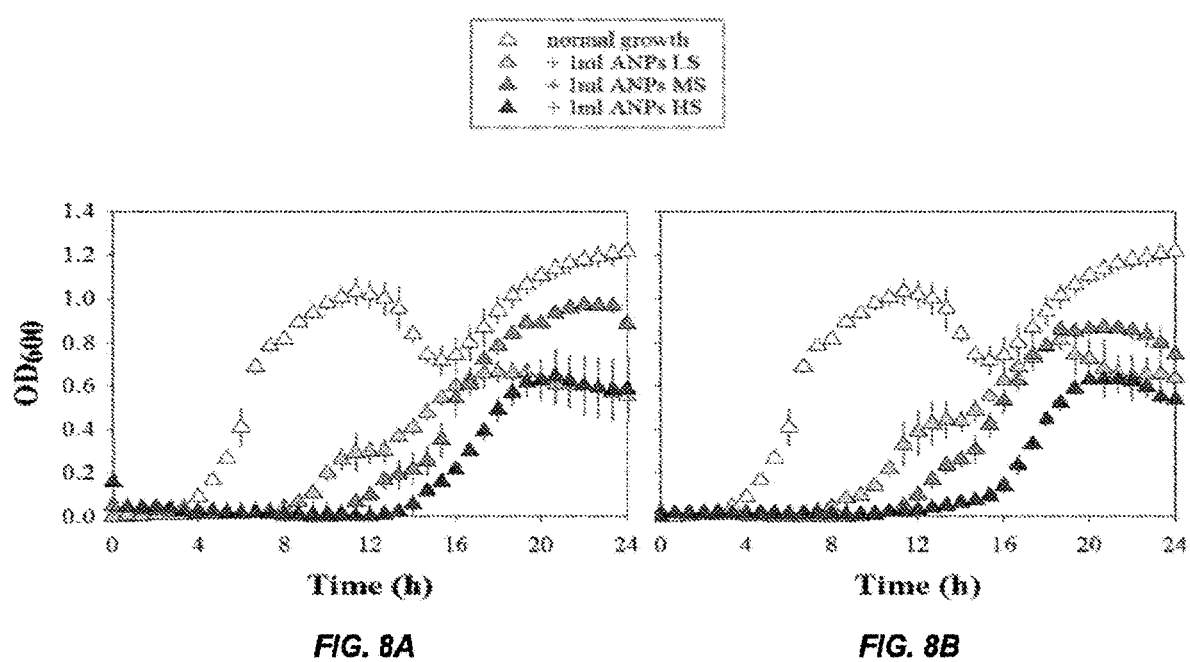
FIGS. 8A and 8B illustrate the growth of *Corynebacterium striatum* in various conditions, including with 1 mL of 45 nm ANPs with LS, MS, and HS (FIG. 8A) or 1 mL of 130 nm ANPs with LS, MS, and HS (FIG. 8B)

*C. striatum* is often resistant to several antibiotics, and it is associated with wound infections, pneumonia, and meningitis. As with *S. aureus* USA300, FIGS. 8A and 8B show that the growth of *C. striatum* was considerably slowed down by ANPs with increasing silver coating on the gold nanospheres. FIG. 8A shows that a 1 mL solution of 45 nm ANPs with low silver delayed onset of the exponential growth phase (approximately 4.7 h) and resulted in slower growth with the *C. striatum* culture reaching 55% of the maximum expected OD, that a 1 mL medium silver ANPs solution similarly delayed the onset of the exponential growth phase (approximately 7.5 h) and resulted in slower growth with the *C. striatum* culture reaching 80% of the maximum expected OD, and that a 1 mL high silver ANPs solution delayed the onset of the exponential growth phase (approximately 10.5 h) and resulted in slower growth with the *C. striatum* culture reaching 53% of the maximum expected OD.

FIG. 8B shows that a 1 mL 130 nm low silver ANPs solution delayed the onset of the exponential growth phase (approximately 5.0 h) and resulted in slower growth with the *C. striatum* culture reaching 67% of the maximum expected OD, that a 1 mL medium silver ANPs solution delayed the onset of the exponential growth phase (approximately 8.7 h) and resulted in slower growth with the *C. striatum* culture reaching 710% of the maximum expected OD, and that a 1 mL high silver ANPs solution delayed the onset of the exponential growth phase (approximately 10.5 h) and resulted in slower growth with the *C. striatum* culture reaching 52% of the maximum expected OD.

Figure 9A:
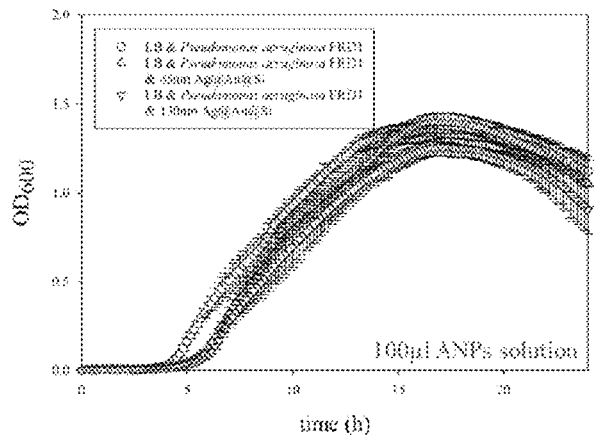
FIGS. 9A and 9B illustrate the growth of *Pseudomonas aeruginosa* FRD1 in various conditions, including with 0.1 mL of 45 nm and 130 nm ANPs with MS (FIG. 9A) and 0.5 mL of 45 nm and 130 nm ANPs with MS (FIG. 9B)
Figure 9B:
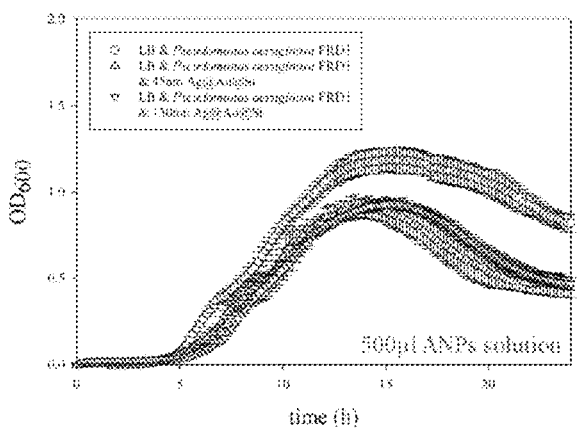

*Pseudomonas aeruginosa* FRD1 is a mucoid strain originally isolated from a chronically infected cystic fibrosis patient with the ability to overproduce exopolymeric alginates, favorable for biofilm formation. FIGS. 9A and 9B show that *P. aeruginosa* FRD1 also presented a strong sensitivity towards higher concentrations of ANPs of the medium silver coating, which can cause slower growth and had a maximum OD that was a fraction of the maximum expected OD. FIG. 9A, for example, shows that 0.1 mL 45 nm & 130 nm ANPs medium silver solutions delayed the onset of the exponential growth phase (approximately 1 h) by *P. aeruginosa* FRD1. FIG. 9B shows, for example, that 0.5 mL 45 nm & 130 nm ANPs medium silver solutions caused slower growth with the *P. aeruginosa* FRD1 culture reaching 75% (for 45 nm) and 79% (for 130 nm) of the maximum expected OD.

Figure 10A:
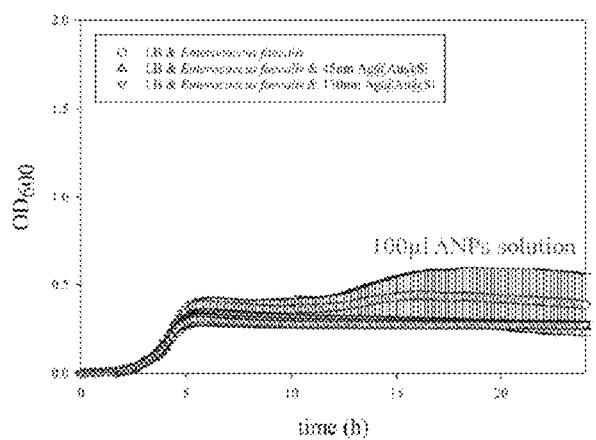
FIG. 10A illustrates the growth of *Enterococcus faecalis* with 0.1 mL of 45 nm and 130 nm ANPs with MS.
Figure 10B:
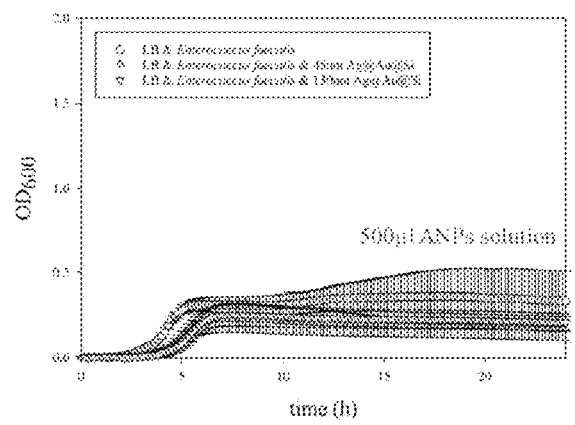
FIG. 10B illustrates the growth of *Enterococcus faecalis* with 0.5 mL of 45 nm and 130 nm ANPs with MS.

*Enterococcus faecalis* can cause endocarditis, septicemia, urinary tract infections, and meningitis. Of the four species tested in FIG. 7-10, *E. faecalis* appears to be the most sensitive to treatment by the disclosed ANPs. As shown in FIGS. 10A and 10B, for example, ANPs containing medium silver appear to slow growth rate of *E. faecalis* and reduced the maximum observed OD to a fraction of the maximum expected OD in comparison to the normal, unstressed growth of the *E. faecalis* culture. FIG. 10A shows that 0.1 mL 45 nm & 130 nm ANPs medium silver solutions resulted in the *E. faecalis* culture reaching only 75% of the maximum expected OD, and FIG. 10B shows that 0.5 mL 45 nm & 130 nm ANPs medium silver solutions delayed the onset of the exponential growth phase (approximately 1 h) and resulted in slower growth with the *E. faecalis* culture reaching 75% (for 45 nm) and 82% (for 130 nm) of the expected maximum OD.

Figure 11A:
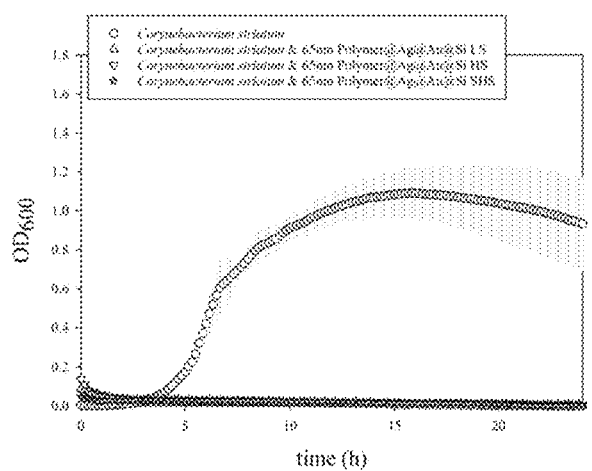
FIG. 11A illustrates the growth of *Corynebacterium striatum* with 65 nm ANPs with various silver concentrations conjugated to a polycationic polymer.
Figure 11B:
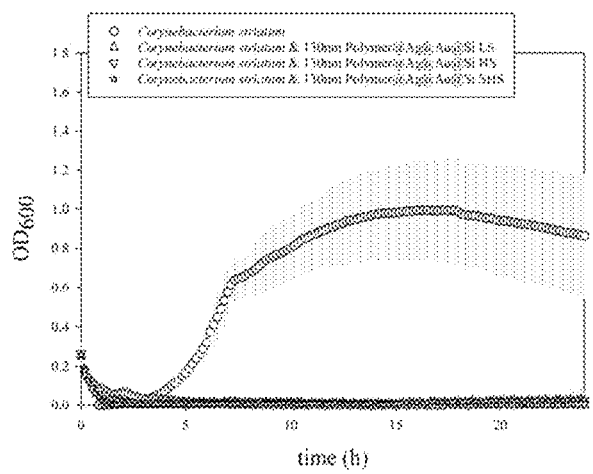
FIG. 11B illustrates the growth of *Corynebacterium striatum* with 130 nm ANPs with various silver concentrations conjugated to a polycationic polymer.

Referring now to FIGS. 11A and 11B, illustrated are growth curves of *Corynebacterium* striatum cultured with 65 nm ANPs with various silver concentrations conjugated to a polycationic polymer (FIG. 11A) and 130 nm ANPs with various silver concentrations conjugated to a polycationic polymer (FIG. 11B). *C. striatum* was pre-cultured at 37° C. for 12 hours in the nutrient rich lysogeny broth (LB) media prior to incubation and measurement with the plate reader (i.e., OD measurement device). Media (6 mL), ANP solutions, and microbial pre-culture (0.01 mL) were mixed within a growth tube and 0.2 mL of samples were directly pipetted into a 96-well plate. The plate was incubated at 37° C. for 24 hours under continuous shaking. Starting OD$_{600}$ cell density measurements were taken.

Interestingly, *C. striatum* responded to the incubation with Polymer@Ag@Au@SiO$_2$ ANPs with complete cell death (i.e., no growth), which indicates that presenting a mixed surface through controlled surface architecture and controlled charged distribution (e.g., by using polycationic polymers) may show high potency to specific bacterial species.

Figure 12A:
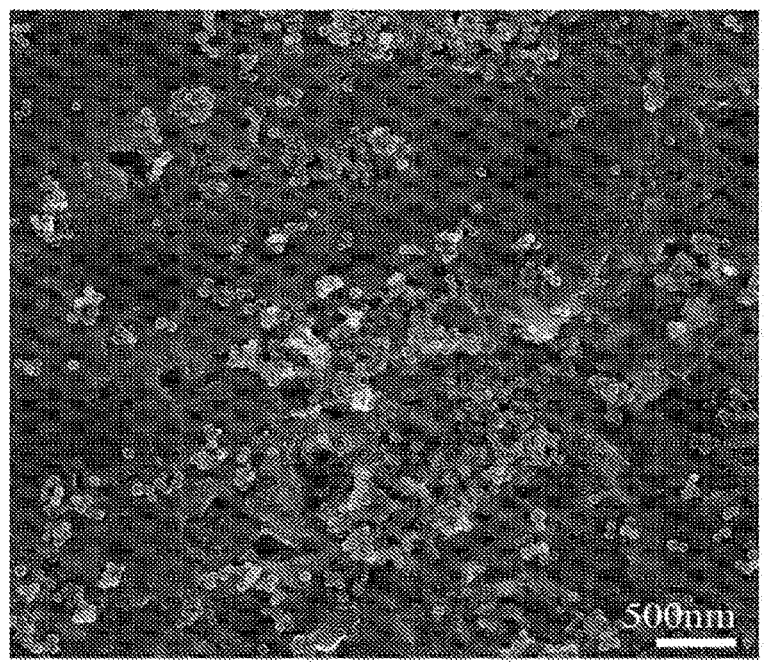
FIG. 12A illustrates a scanning electron micrograph (SEM) image of ANPs conjugated to a polycationic polymer immobilized on an implant-grade metal surface.
Figure 12B:
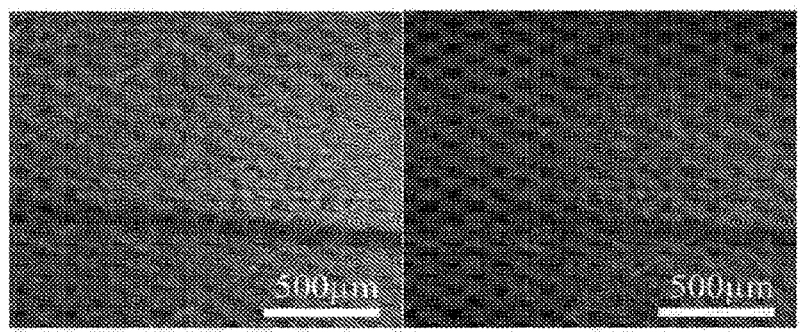
FIG. 12B illustrates images of simultaneous green (left) and red (right) fluorescence of ANPs conjugated to a polycationic polymer immobilized on an implant-grade metal surface where only green fluorescence indicates viable bacteria and simultaneous green and red fluorescence from the same location indicates non-viable bacteria.

Furthermore, it should be noted that ANPs@Polymer immobilized on an implant grade metal surface (e.g., for medical implants) have unexpectedly exhibited >99.99% bactericidal effect against antibiotic-resistant *S. aureus*, confirmed by scanning electron micrography and simultaneous green and red fluorescence from the 'Bacteria Live/Dead' fluorescent assay, represented in FIGS. 12A and 12B.

Figure 13:
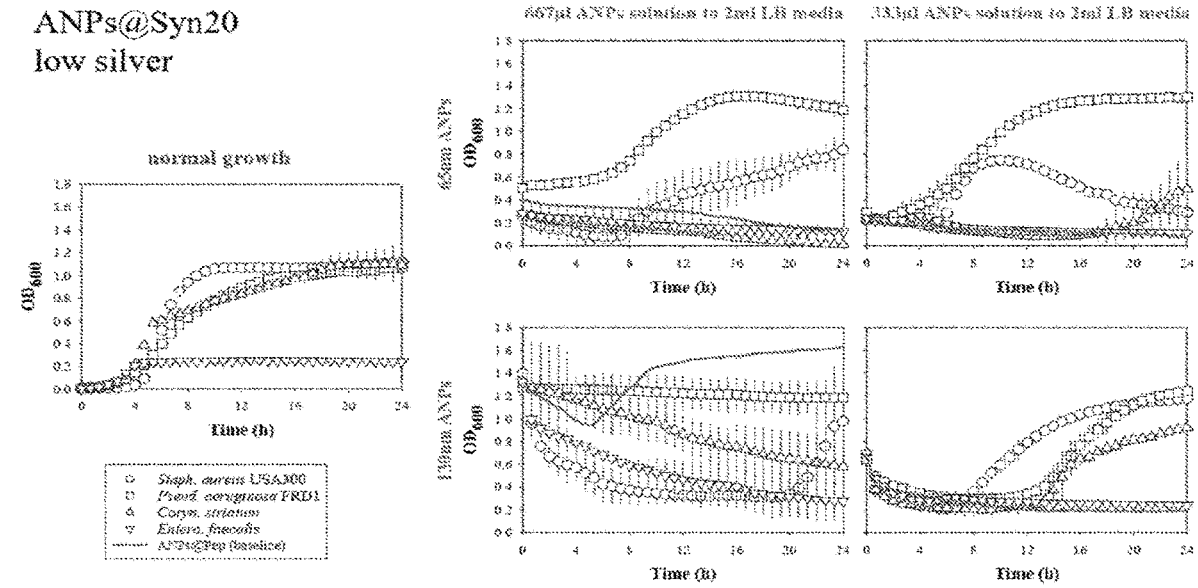
FIG. 13 illustrates the growth of various pathogens with various concentrations of 65 nm and 130 nm ANPs with LS conjugated to synthetic safencin-20.
Figure 14:
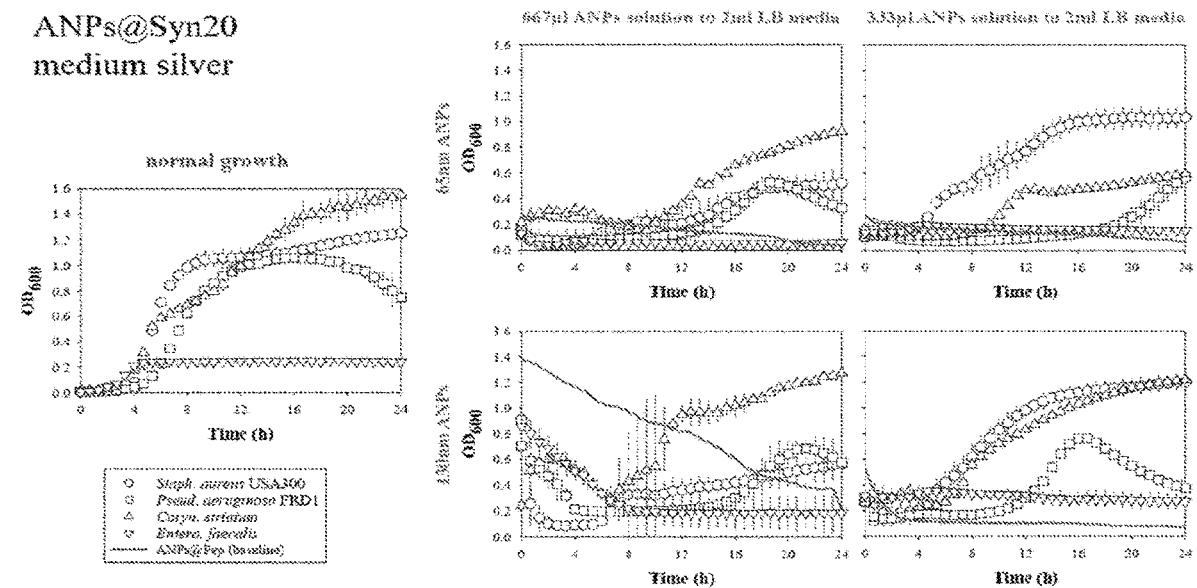
FIG. 14 illustrates the growth of various pathogens with various concentrations of 65 nm and 130 nm ANPs with MS conjugated to synthetic safencin-20.
Figure 15:
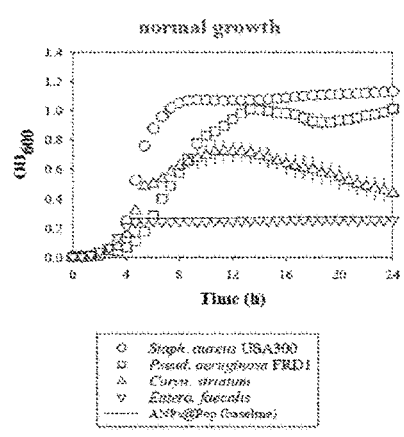
FIG. 15 illustrates the growth of various pathogens with various concentrations of 65 nm and 130 nm ANPs with HS conjugated to synthetic safencin-20.
Figure 15:
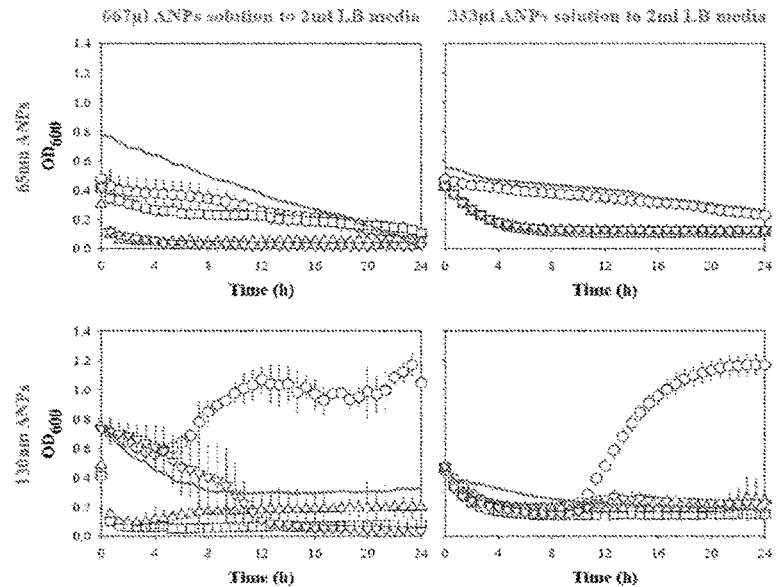
Figure 16:
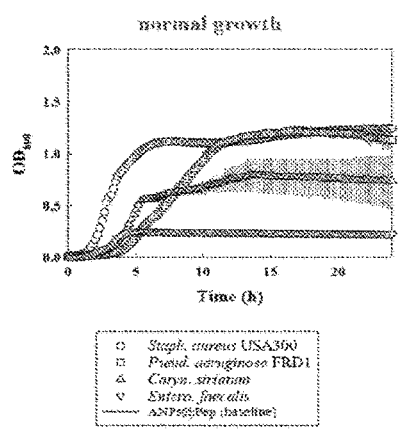
FIG. 16 illustrates the growth of various pathogens with various concentrations of 65 nm and 130 nm ANPs with LS conjugated to mutant chensinin-1-2.
Figure 16:
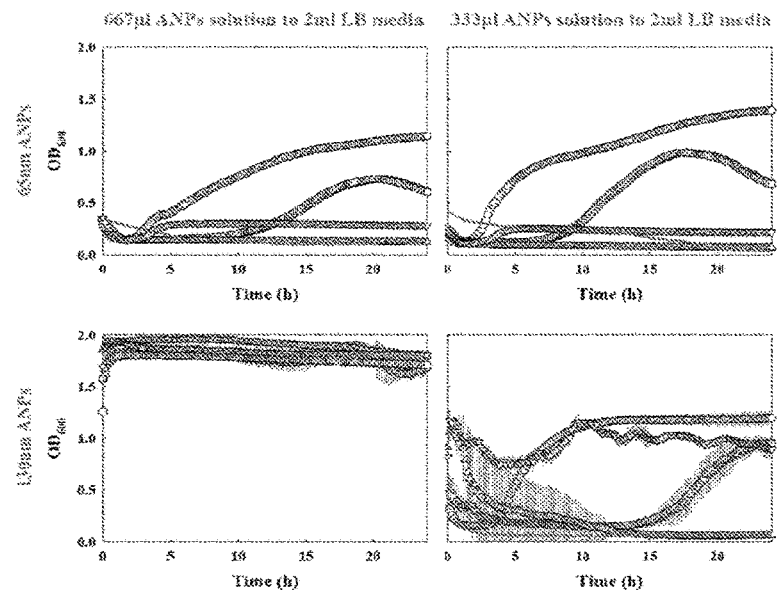
Figure 17:
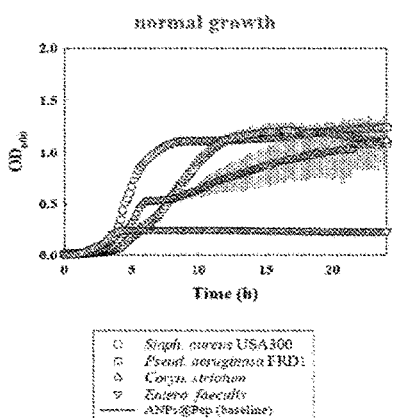
FIG. 17 illustrates the growth of various pathogens with various concentrations of 65 nm and 130 nm ANPs with MS conjugated to mutant chensinin-1-2.
Figure 17:
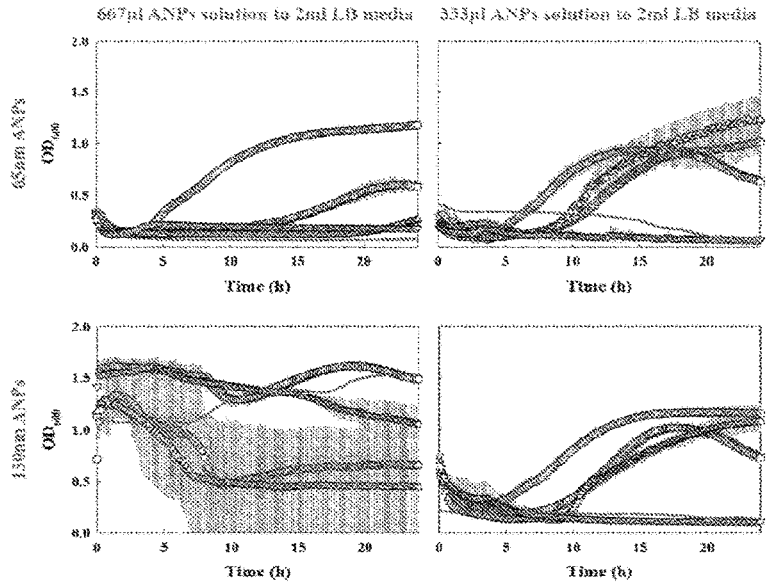
Figure 18:
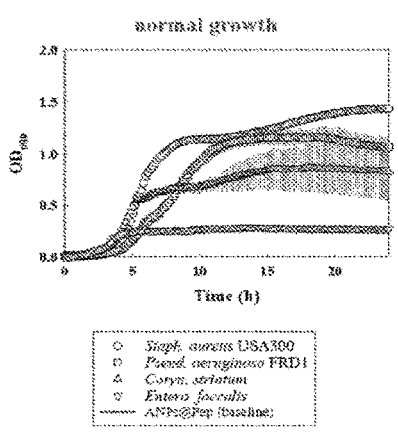
FIG. 18 illustrates the growth of various pathogens with various concentrations of 65 nm and 130 nm ANPs with HS conjugated to mutant chensinin-1-2.
Figure 18:
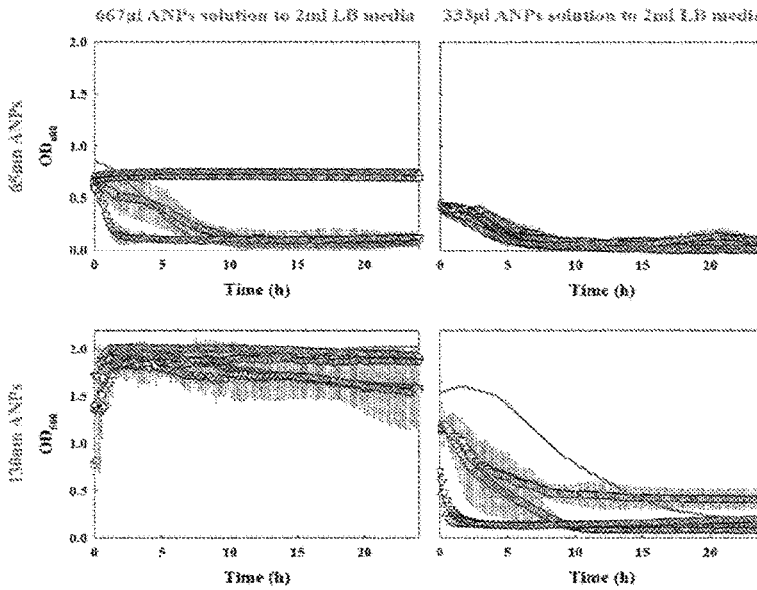

FIG. 13-15 illustrate the growth of *S. aureus* USA300, *P. aeruginosa* FRD1, *C. striatum*, and *E. faecalis* when incubated with various concentrations of ANPs conjugated to synthetic safencin-20 (ANPs@Syn20). FIG. 16-18 illustrate the growth of *S. aureus* USA300, *P. aeruginosa* FRD1, *C. striatum*, and *E. faecalis* when incubated with various concentrations of ANPs conjugated to mutant chensinin-1-2 (ANPs@MC1-2). Pre-cultures of the four bacteria were grown for 12 hours at 37° C. in LB broth to about 1×10$^7$ CFU/mL. For the bactericidal test, the bacteria were incubated in LB broth with two concentrations of ANPs@AMPs (low and high concentration, for both Syn20 and MC1-2 in separate tests) for 24 hours at 37° C. in a 96 well plate under continuous shaking.

At least three or more replications were performed for each condition. The solid curves represent the baseline of ANPs@AMPs in LB broth as a control. The normal growth curves represent the respective bacterial species growth in LB broth. All other curves represent respective bacterial species grown in LB broth containing ANPs@AMPs. As is evident from FIG. 13-18, in many instances, the ANPs@AMPs exhibited bactericidal effects by inhibiting growth and/or killing each tested bacterial species, especially ANPs@MC1-2 high silver, which, in some instances, exhibited broad-spectrum antimicrobial activity with >99.9% kill rate against all four tested pathogens. In such implementations, the peptide concentration of ANPs@MC1-2 was approximately ten times lower than the concentration of free MC1-2 peptides required to achieve similar results. Accordingly, by controlling the steric presentation of the peptides immobilized on the surface of the ANPs, as provided by ANPs disclosed herein, an increased efficacy of the antibacterial peptides is attainable while simultaneously decreasing material costs.

Exemplary Methods and Applications

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 19:
FIG. 19 illustrates an exemplary flow diagram depicting a method for creating an antibacterial nanoparticle, according to the present disclosure.

FIG. 19 illustrates an exemplary flow diagram 1900 depicting a method for creating an antibacterial nanoparticle. Flow diagram 1900 depicts acts of synthesizing a silica core (1902), synthesizing a plurality of gold nanospheres (1904), immobilizing the plurality of gold nanospheres on the silica core (1906), coating the gold nanospheres with a layer of silver (1908), immobilizing a plurality of iron oxide nanospheres on the silica core (1910), conjugating peptides to the silver-coated gold nanospheres and/or the iron oxide nanospheres (1912), and anchoring fluorescein molecules to the silver-coated nanospheres (1914). It should be noted that not all of the foregoing acts are necessary to create an antibacterial nanoparticle, according to the present disclosure. For example, an antibacterial nanoparticle may omit iron oxide nanospheres, peptides, and/or fluorescein molecules, and therefore acts 1910, 1912, and/or 1914 may be omitted.

As noted above, act 1902 includes synthesizing a silica core. As noted above, a silica core may be synthesized, for example, by a sol-gel method (e.g., the Stöber process) involving hydrolysis and condensation of TEOS. In some instances, the silica core has a diameter within a range of 25 nm to 150 nm. It will be appreciated, however, that the synthesizing a silica core is not an essential aspect of the present disclosure, and a silica core may be simply obtained rather than synthesized in accordance with the method represented in flow diagram 1900.

Act 1904 includes synthesizing a plurality of gold nanospheres. As described above, gold nanospheres may be formed by alkaline reduction (e.g., at room temperature). In some embodiments, the gold nanospheres have a diameter within a range of 3 nm to 10 nm. It will be appreciated, however, that the synthesizing a plurality of gold nanospheres is not an essential aspect of the present disclosure, and gold nanospheres may be simply obtained rather than synthesized in accordance with the method represented in flow diagram 1900.

Act 1906 includes immobilizing the plurality of gold nanospheres on the silica core. For instance, the gold nanospheres may be mixed into a prepared $SiO_2$-APTES cores solution and covered with stirring for approximately eight hours or more. In some embodiments, the gold nanospheres are conjugated to the silica core 100 such that the ratio of the silica core diameter to the distance between the gold nanospheres is within a range of 2 to 4, or greater than 4 (e.g., 8 to 15).

Act 1908 includes coating the gold nanospheres with a layer of silver. In some implementations, 10 mM $AgNO_3$ and 10 mM hydroquinone solution is mixed with the gold nanospheres disposed on the silica core. Various silver concentrations are within the scope of this disclosure, and the silver concentration may be varied by utilizing different proportions of $AgNO_3$ and hydroquinone solution.

Act 1910 includes immobilizing a plurality of iron oxide nanospheres on the silica core. In some embodiments, the iron oxide nanospheres have a diameter within a range of 3 nm to 10 nm. The iron oxide nanospheres may be conjugated to the silica core by being directly fused thereto or by being linked to the silica core using carbodiimide chemistry. The iron oxide nanospheres may be interspersed between the discontinuous shell of the silver-alloyed gold nanospheres. In some implementations, the iron oxide nanospheres generate a magnetic hyperthermia inducing shell around the silica core.

Act 1912 includes conjugating peptides to the silver-coated gold nanospheres and/or the iron oxide nanospheres. In some instances, the peptides are joined to the nanospheres by a linking group, such as a silane or a thiol group. The peptides may include, for example, antimicrobial peptides, such as MC1-2, Syn20, and/or Syn96, conjugated to the silver-coated gold nanospheres. Additionally, or alternatively, the peptides may include cell penetrating peptides conjugated to the iron oxide nanospheres, if any.

Act 1914 includes anchoring fluorescein molecules to the silver-coated nanospheres. In some implementations, fluorescein molecules are linked by a cephalosporin linker, or a thiol linker, to the nanospheres. The fluorescein molecules may avoid metal quenching caused by the metals of the ANP when disassociated from the ANP (e.g., by bacterial enzymes) and become usable for fluorescence detection methods to detect the presence of a bacterial infection.

It should be appreciated that different linkers can be bound to different fluorescent molecules with each linker being susceptible to degradation by a specific bacterium. In this manner, the fluorescence color signals emitted from the sample can be used as a quasi-diagnostic tool for quickly identifying different strains of bacteria present in the infection or sample.

A modular ANP created according to at least some of the acts represented in flow diagram 1900 will include various combinations of gold nanospheres, iron oxide nanospheres, silver coating, peptides, and/or fluorescein molecules disposed on a $SiO_2$ core. Because of their biocompatibility, as discussed hereinabove, ANPs of the present disclosure may be implemented into various medical products. For example, as noted above, Polymer@Ag@Au@$SiO_2$ ANPs may exhibit >99.99% bactericidal effect against *S. aureus* when disposed on an implant-grade metal surface. In other instances, ANPs are coated and/or printed (e.g., by chemisorption using silane or thiol or by click chemistry) on the surface(s) of medical implants, such as permanent implants including, but not limited to, orthopedic implants, pacemakers, and/or dental implants, or temporary implants including, but not limited to, catheters, cannulas, and/or drainage materials. Furthermore, ANPs may be coated and/or printed on surgical and/or dental instruments and provided as part of a pre-sterilized kit, which may prove particularly useful in non-hospital environments where tools are not kept sterile on-site (e.g., for use by first responders in hazardous environments). Additionally, the ANPs of the present disclosure may be added to a topological cream (e.g., an ointment or cosmetic cream) for treating bacterial infections by coming into contact with the bacteria.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. An antibacterial nanoparticle, comprising:
   a silica core;
   a plurality of silver-coated gold nanospheres conjugated to the silica core; and
   optionally a plurality of iron oxide nanospheres conjugated to the silica core, wherein at least some of the plurality of silver-coated gold nanospheres, or at least some of the plurality of iron oxide nanospheres, if any, are conjugated to one or more polycationic polymers and/or one or more antibacterial peptides.

2. The antibacterial nanoparticle of claim 1, further comprising a plurality of iron oxide nanospheres conjugated to the silica core, wherein a surface density of the plurality of iron oxide nanospheres on the silica core is at least 60% similar to a surface density of protein turrets on a bacteriophage, preferably above 80%.

3. The antibacterial nanoparticle of claim 1, wherein a surface density of the plurality of silver-coated gold nanospheres on the silica core is at least 60% similar to a surface density of protein turrets on a bacteriophage, preferably above 80%.

4. The antibacterial nanoparticle of claim 1, wherein the one or more antibacterial peptides include at least one of mutant chensinin-1-2 (SEQ ID NO: 1), synthetic safencin-20 (SEQ ID NO: 2), synthetic safencin-96 (SEQ ID NO: 3), synthetic safencin (SEQ ID NO: 4), peptide 20 (SEQ ID NO: 5), peptide 52 (SEQ ID NO: 6), peptide 60 (SEQ ID NO: 7), peptide 90 (SEQ ID NO: 8), peptide 91 (SEQ ID NO: 9), peptide 92 (SEQ ID NO: 10), peptide 93 (SEQ ID NO: 11), peptide 94 (SEQ ID NO: 12), or peptide 96 (SEQ ID NO: 13).

5. The antibacterial nanoparticle of claim 1, wherein the plurality of silver-coated gold nanospheres include a medium silver coating or a high silver coating and at least some of the plurality of silver-coated gold nanospheres, or at least some of the plurality of iron oxide nanospheres, if any, are conjugated to mutant chensinin-1-2 (SEQ ID NO: 1) and/or synthetic safencin-20 (SEQ ID NO: 2).

6. The antibacterial nanoparticle of claim 1, further comprising a fluorescein molecule anchored to at least some of the silver-coated gold nanospheres.

7. The antibacterial nanoparticle of claim 1, further comprising a cell penetrating peptide anchored to at least some of the iron oxide nanospheres.

8. An antibacterial medical product, comprising a plurality of antibacterial nanoparticles according to claim 1.

9. The antibacterial medical product of claim 8, wherein the plurality of antibacterial nanoparticles is disposed on a medical or dental implant.

10. The antibacterial medical product of claim 8, wherein the plurality of antibacterial nanoparticles is disposed on a surgical instrument.

11. The antibacterial medical product of claim 8, wherein the plurality of antibacterial nanoparticles is added to a topological cream.

12. A method for creating an antibacterial nanoparticle, the method comprising:
    immobilizing a plurality of gold nanospheres on a silica core;
    coating at least a portion of the plurality of gold nanospheres with a layer of silver;
    optionally immobilizing a plurality of iron oxide nanospheres on the silica core; and
    conjugating one or more antibacterial peptides to the silver-coated gold nanospheres, or the iron oxide nanospheres, if any.

13. The method of claim 12, wherein coating the portion of the plurality of gold nanospheres with the layer of silver comprises coating with a low level of silver, a medium level of silver, or a high level of silver.

14. The method of claim 12, wherein conjugating the one or more antibacterial peptides to the silver-coated gold nanospheres, or the iron oxide nanospheres, if any, comprises conjugating at least one of mutant chensinin-1-2 (SEQ ID NO: 1), synthetic safencin-20 (SEQ ID NO: 2), synthetic safencin-96 (SEQ ID NO: 3), synthetic safencin (SEQ ID NO: 4), peptide 20 (SEQ ID NO: 5), peptide 52 (SEQ ID NO: 6), peptide 60 (SEQ ID NO: 7), peptide 90 (SEQ ID NO: 8), peptide 91 (SEQ ID NO: 9), peptide 92 (SEQ ID NO: 10), peptide 93 (SEQ ID NO: 11), peptide 94 (SEQ ID NO: 12), or peptide 96 (SEQ ID NO: 13).

15. The method of claim 12, further comprising anchoring one or more fluorescein nanospheres to the silver-coated gold nanospheres.

* * * * *

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: synthetic antimicrobial peptide: mutant
      chensinin-1-2

<400> SEQUENCE: 1

Ser Ala Val Trp Arg Trp Arg Arg Phe Trp Leu Arg Lys Arg Lys
1               5                   10                  15

<210> SEQ ID NO 2
<211> LENGTH: 25
<212> TYPE: PRT
<213> ORGANISM: Artificial Sequence
<220> FEATURE:
<223> OTHER INFORMATION: synthetic antimicrobial peptide: safencin-20

<400> SEQUENCE: 2

Ala Trp Lys Lys Thr Ile Arg Gln Tyr Leu Lys Asn Lys Ile Lys Lys
1               5                   10                  15

Lys Gly Arg Lys Ala Val Ile Ala Trp
            20                  25

<210> SEQ ID NO 3
<211> LENGTH: 25
<212> TYPE: PRT
<213> ORGANISM: Artificial Sequence
<220> FEATURE:
<223> OTHER INFORMATION: synthetic antimicrobial peptide: safencin-96

<400> SEQUENCE: 3

Ala Trp Lys Glu Lys Ile Arg Lys Lys Leu Lys Asn Glu Ile Lys Lys
1               5                   10                  15

Lys Trp Arg Lys Ala Val Ile Ala Trp
            20                  25

<210> SEQ ID NO 4
```

```
<211> LENGTH: 25
<212> TYPE: PRT
<213> ORGANISM: Artificial Sequence
<220> FEATURE:
<223> OTHER INFORMATION: synthetic antimicrobial peptide: safencin

<400> SEQUENCE: 4

Ala Gly Lys Glu Thr Ile Arg Gln Tyr Leu Lys Asn Glu Ile Lys Lys
1               5                   10                  15

Lys Gly Arg Lys Ala Val Ile Ala Trp
            20                  25

<210> SEQ ID NO 5
<211> LENGTH: 25
<212> TYPE: PRT
<213> ORGANISM: Artificial Sequence
<220> FEATURE:
<223> OTHER INFORMATION: synthetic antimicrobial peptide: peptide 20

<400> SEQUENCE: 5

Ala Trp Lys Lys Thr Ile Arg Gln Tyr Leu Lys Asn Lys Ile Lys Lys
1               5                   10                  15

Lys Gly Arg Lys Ala Val Ile Ala Trp
            20                  25

<210> SEQ ID NO 6
<211> LENGTH: 25
<212> TYPE: PRT
<213> ORGANISM: Artificial Sequence
<220> FEATURE:
<223> OTHER INFORMATION: synthetic antimicrobial peptide: peptide 52

<400> SEQUENCE: 6

Ala Gly Lys Lys Thr Ile Arg Gln Tyr Leu Lys Asn Lys Ile Lys Lys
1               5                   10                  15

Lys Trp Arg Lys Ala Val Ile Ala Trp
            20                  25

<210> SEQ ID NO 7
<211> LENGTH: 25
<212> TYPE: PRT
<213> ORGANISM: Artificial Sequence
<220> FEATURE:
<223> OTHER INFORMATION: synthetic antimicrobial peptide: peptide 60

<400> SEQUENCE: 7

Ala Gly Lys Lys Thr Ile Arg Gln Tyr Leu Lys Asn Lys Ile Lys Lys
1               5                   10                  15

Lys Gly Arg Lys Trp Val Ile Ala Trp
            20                  25

<210> SEQ ID NO 8
<211> LENGTH: 25
<212> TYPE: PRT
<213> ORGANISM: Artificial Sequence
<220> FEATURE:
<223> OTHER INFORMATION: synthetic antimicrobial peptide: peptide 90

<400> SEQUENCE: 8

Ala Trp Lys Lys Thr Ile Arg Gln Tyr Leu Lys Asn Glu Ile Lys Lys
1               5                   10                  15

Lys Trp Arg Lys Ala Val Ile Ala Trp
            20                  25
```

```
<210> SEQ ID NO 9
<211> LENGTH: 25
<212> TYPE: PRT
<213> ORGANISM: Artificial Sequence
<220> FEATURE:
<223> OTHER INFORMATION: synthetic antimicrobial peptide: peptide 91

<400> SEQUENCE: 9

Ala Trp Lys Glu Thr Ile Arg Gln Tyr Leu Lys Asn Lys Ile Lys Lys
1               5                   10                  15

Lys Trp Arg Lys Ala Val Ile Ala Trp
            20                  25

<210> SEQ ID NO 10
<211> LENGTH: 25
<212> TYPE: PRT
<213> ORGANISM: Artificial Sequence
<220> FEATURE:
<223> OTHER INFORMATION: synthetic antimicrobial peptide: peptide 92

<400> SEQUENCE: 10

Ala Trp Lys Lys Thr Ile Arg Gln Tyr Leu Lys Asn Lys Ile Lys Lys
1               5                   10                  15

Lys Trp Arg Lys Ala Val Ile Ala Trp
            20                  25

<210> SEQ ID NO 11
<211> LENGTH: 25
<212> TYPE: PRT
<213> ORGANISM: Artificial Sequence
<220> FEATURE:
<223> OTHER INFORMATION: synthetic antimicrobial peptide: peptide 93

<400> SEQUENCE: 11

Ala Trp Lys Glu Lys Ile Arg Gln Tyr Leu Lys Asn Glu Ile Lys Lys
1               5                   10                  15

Lys Trp Arg Lys Ala Val Ile Ala Trp
            20                  25

<210> SEQ ID NO 12
<211> LENGTH: 25
<212> TYPE: PRT
<213> ORGANISM: Artificial Sequence
<220> FEATURE:
<223> OTHER INFORMATION: synthetic antimicrobial peptide: peptide 94

<400> SEQUENCE: 12

Ala Trp Lys Glu Thr Ile Arg Lys Tyr Leu Lys Asn Glu Ile Lys Lys
1               5                   10                  15

Lys Trp Arg Lys Ala Val Ile Ala Trp
            20                  25

<210> SEQ ID NO 13
<211> LENGTH: 25
<212> TYPE: PRT
<213> ORGANISM: Artificial Sequence
<220> FEATURE:
<223> OTHER INFORMATION: synthetic antimicrobial peptide: peptide 96

<400> SEQUENCE: 13

Ala Trp Lys Glu Lys Ile Arg Lys Lys Leu Lys Asn Glu Ile Lys Lys
1               5                   10                  15

Lys Trp Arg Lys Ala Val Ile Ala Trp
            20                  25
```